(12) United States Patent
Forsell

(10) Patent No.: US 10,973,641 B2
(45) Date of Patent: Apr. 13, 2021

(54) HIP JOINT DEVICE

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 52 days.

(21) Appl. No.: 15/830,083

(22) Filed: Dec. 4, 2017

(65) Prior Publication Data

US 2018/0185158 A1   Jul. 5, 2018

Related U.S. Application Data

(63) Continuation of application No. 13/382,997, filed as application No. PCT/SE2010/050832 on Jul. 12, 2010, now Pat. No. 9,833,322.

(Continued)

(30) Foreign Application Priority Data

| Jul. 10, 2009 | (SE) | 0900957-2 |
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |
| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |

(Continued)

(51) Int. Cl.
*A61F 2/32* (2006.01)
*A61F 2/34* (2006.01)
(Continued)

(52) U.S. Cl.
CPC .............. *A61F 2/32* (2013.01); *A61F 2/34* (2013.01); *A61F 2/3601* (2013.01);
(Continued)

(58) Field of Classification Search
CPC .............. A61F 2/32; A61F 2002/30378; A61F 2002/30518; A61F 2002/30654; A61F 2002/3233; A61F 2002/3443
See application file for complete search history.

(56) References Cited

U.S. PATENT DOCUMENTS

| 2005/0004678 A1* | 1/2005 | Richards ................ A61F 2/32 |
| | | 623/22.28 |
| 2008/0140215 A1* | 6/2008 | Gladdish ............ A61F 2/30721 |
| | | 623/22.21 |

* cited by examiner

*Primary Examiner* — Christopher D. Prone
*Assistant Examiner* — Christine L Nelson

(57) ABSTRACT

A medical device for implantation in a hip joint comprising: a first part adapted to be fixated to the femoral bone of the patient; and a second part rotatably connected to the first part by means of a connecting member. The first part comprises a bowl-shaped inner contacting surface portion adapted to receive a bowl-shaped outer contacting surface portion of the second part such that the second part is rotatable, relative to the first part, around a point of rotation formed by the connecting member. The second part comprises a bowl-shaped inner surface adapted to receive a ball-shaped portion of a prosthetic replacement for the caput femur. The inner contacting surface comprises at least one extending portion extending beyond the equator line and being adapted to clasp the ball-shaped portion of the prosthetic replacement for the caput femur.

16 Claims, 28 Drawing Sheets

Related U.S. Application Data

(60) Provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009, provisional application No. 61/229,738, filed on Jul. 30, 2009.

(30) Foreign Application Priority Data

| Date | Country | Number |
|---|---|---|
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.
  *A61F 2/36* (2006.01)
  *A61F 2/30* (2006.01)

(52) U.S. Cl.
  CPC . *A61F 2002/305* (2013.01); *A61F 2002/3085* (2013.01); *A61F 2002/30387* (2013.01); *A61F 2002/30495* (2013.01); *A61F 2002/30565* (2013.01); *A61F 2002/30578* (2013.01); *A61F 2002/3233* (2013.01); *A61F 2002/3241* (2013.01); *A61F 2002/3483* (2013.01); *A61F 2002/3493* (2013.01); *A61F 2002/3615* (2013.01)

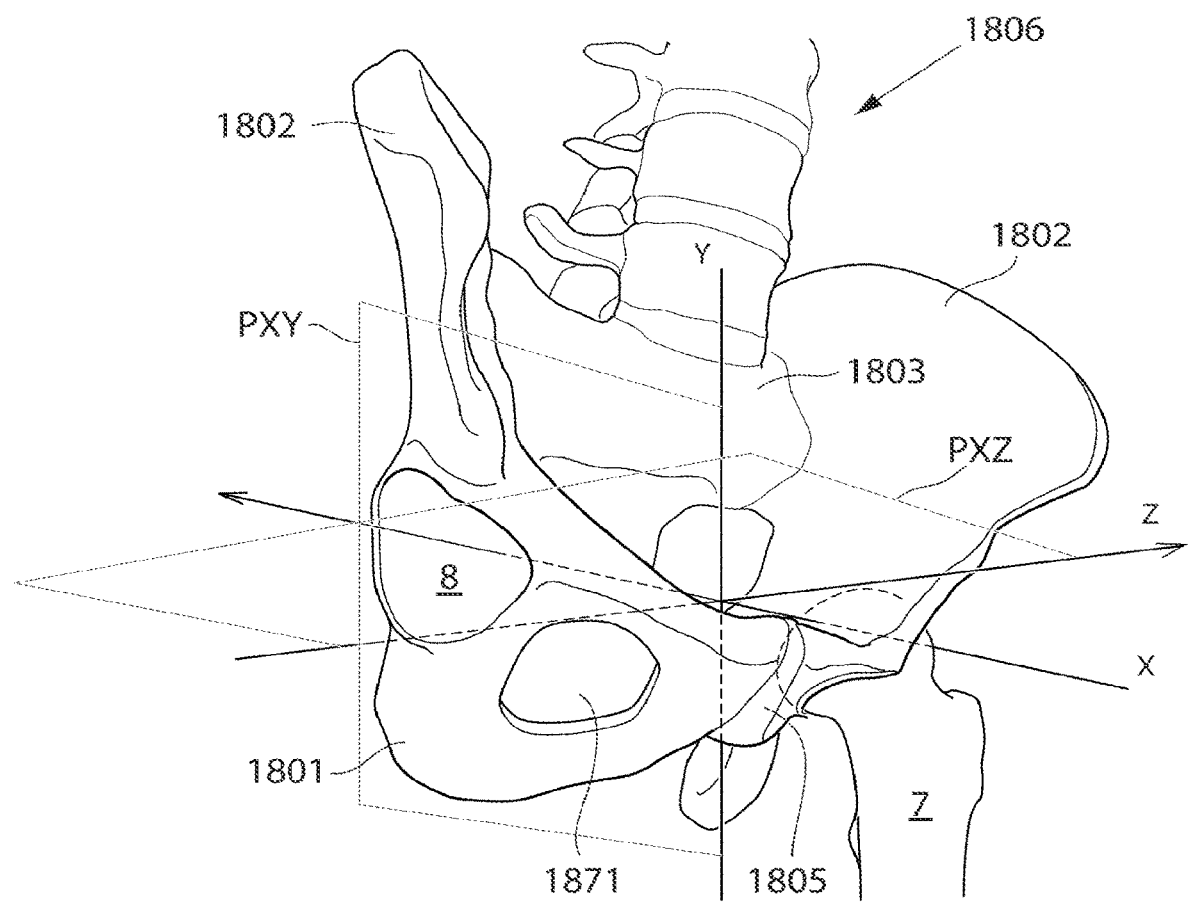

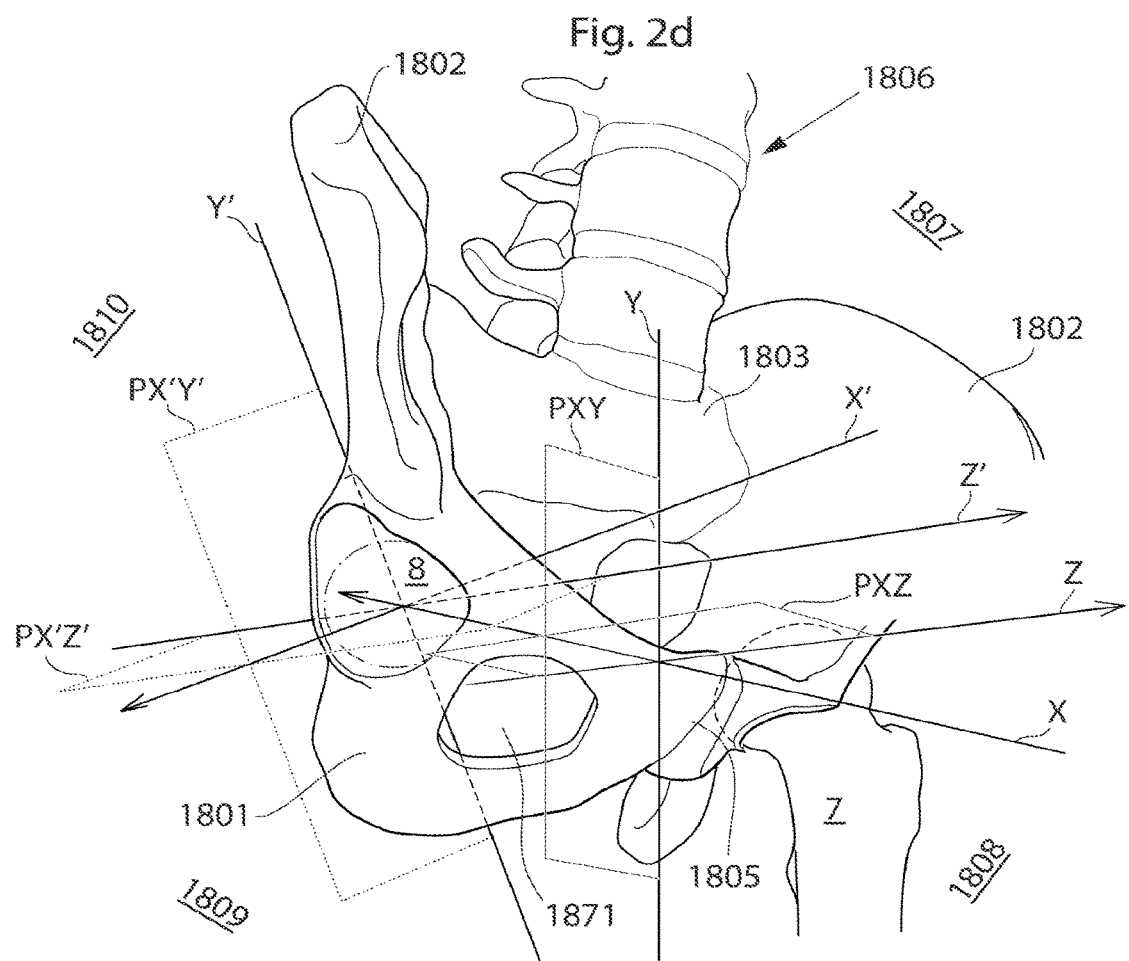
Fig. 2d
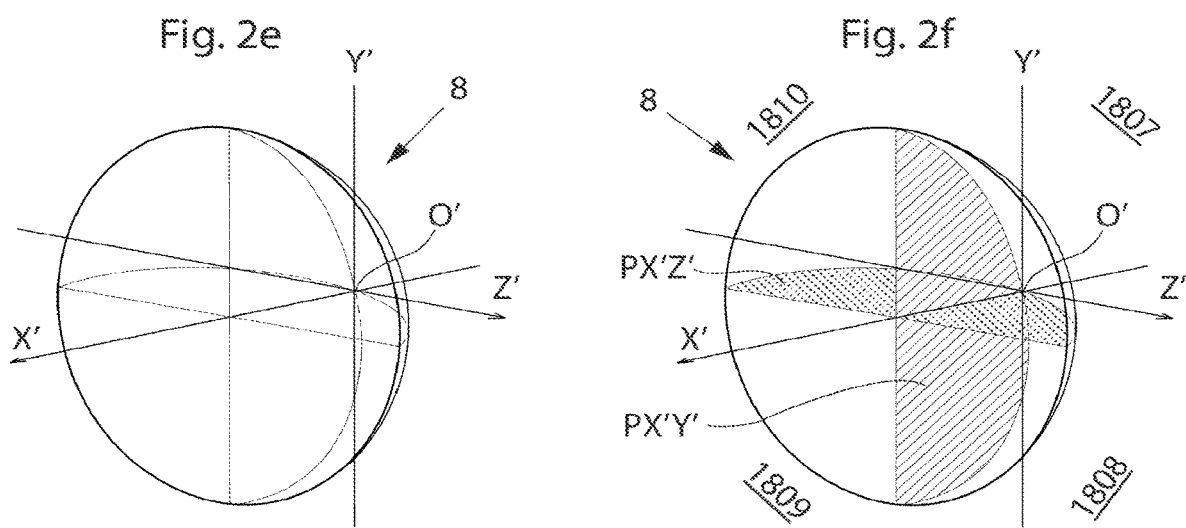
Fig. 2e
Fig. 2f

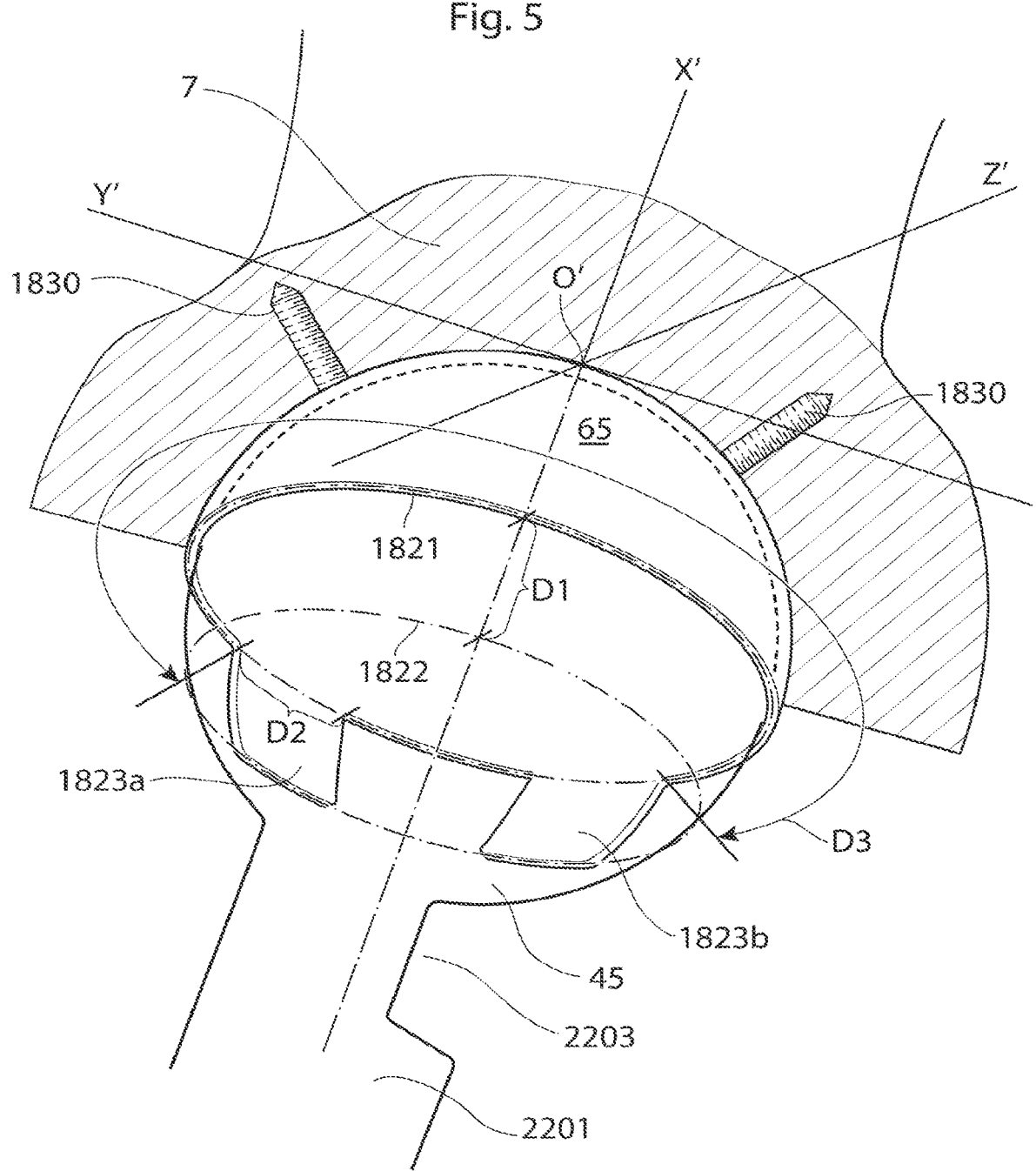

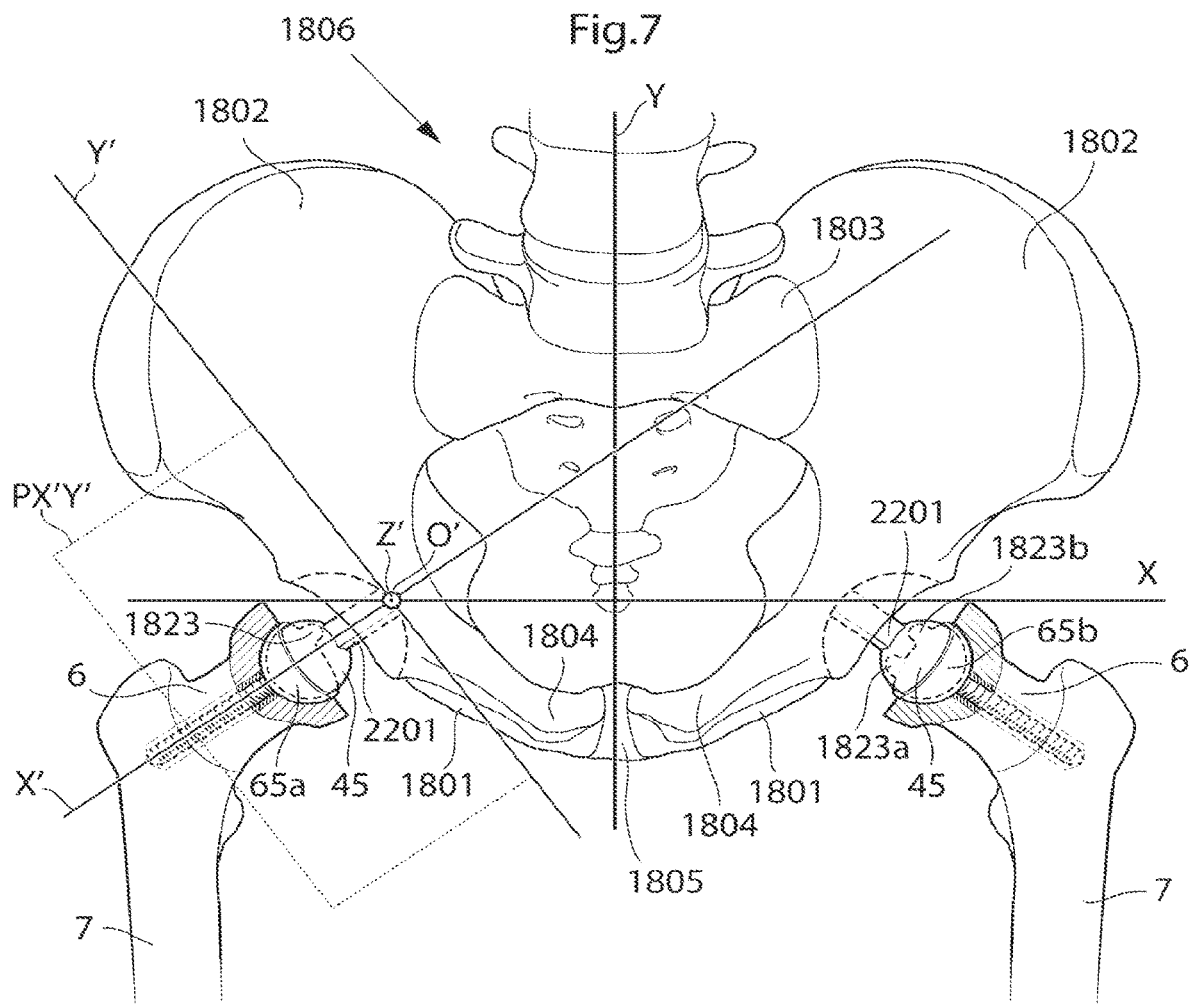
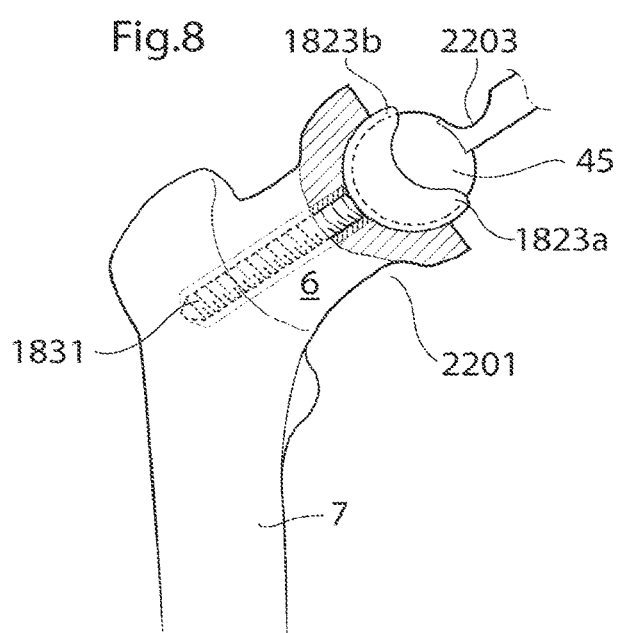

HIP JOINT DEVICE

This application is a continuation of U.S. application Ser. No. 13/382,997, filed Sep. 1, 2012, which is the National Stage Entry of PCT/SE2010/1050832, which claims the benefit of Provisional Application Nos. 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,789, 61/229,796, 61/229,735, 61/229,738, all filed Jul. 30, 2009, and Priority from Swedish Application Nos. 0900958-0, 0900978-8, 0900976-2, 0900974-7, 0900973-9, 0900972-1, 0900970-5, 0900969-7, 0900968-9, 0900966-3, 0900965-5, 0900963-0, 0900962-2, 0900960-6, 0900959-8, 0900957-2, 0900981-2, all filed Jul. 10, 2009, the entire contents of each application is hereby incorporated by reference in this application.

TECHNICAL FIELD

The present invention relates generally to medical devices for implantation in a hip joint.

BACKGROUND ART

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia lata and the lateral muscles of the thigh. To get access by the joint, the supporting Capsule attached ID Femur and Ilium needs to be penetrated, making it difficult to get a fully functional joint after the surgery. Femur is then cut at the neck with a bone saw and the prosthesis is placed in femur either with bone cement or without Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A medical device for implantation in a hip joint of a patient is provided. The medical device is adapted to be fixated to the femoral bone of the patient. The medical device comprises an inner and an outer surface, wherein a contacting portion of said inner surface is spherical and adapted to face the center of the hip joint when said medical device is implanted, and wherein said medical device is adapted to receive a prosthetic replacement for the caput femur fixated to the pelvic bone having a spherical portion. The medical device comprises at least one extending portion, extending said contacting portion of said inner surface such that said at least one extending portion clasps said spherical portion of said prosthetic replacement for the caput femur, such that said spherical portion is restrained in said medical device.

According to one embodiment, the medical device is adapted to receive a prosthetic replacement for the caput femur having a spherical portion, wherein said prosthetic replacement for the caput femur is adapted to be fixated to the pelvic bone by a connection via an elongated portion fixated to said spherical portion of said prosthetic caput femur. The inner surface comprises an equator line, being the largest circular circumference of said inner contacting surface, being a surface adapted to be in contact with said caput femur, or prosthetic replacement therefor, and the at least one extending portion passes beyond said equator line, such that the end portion of said contacting portion of said inner surface forms a circular extension line having a smaller circumference than said equator line. The at least one extending portion circumferentially extends discontinuously along said equator line, such that a portion of said elongated member can be placed between said extension line and said equator line.

A medical device for implantation in a hip joint is further provided. The medical device is adapted to be fixated to the femoral bone and receive a prosthetic replacement for the caput femur having a spherical portion, wherein said prosthetic replacement for the caput femur is adapted to be fixated to the pelvic bone by a connection via an elongated portion fixated to said spherical portion of said prosthetic caput femur. An inner surface comprises an equator line, being the largest circular circumference of said inner surface, at least one extending portion passes beyond said equator line, such that the end portion of said contacting portion of said inner surface forms a circular extension line having a smaller circumference than said equator line, and said at least one extending portion circumferentially extends discontinuously along said equator line, such that a portion of said elongated member can be placed between said extension line and said equator line.

According to one embodiment, said extension line is placed dorsal to the equator line, when the medical device is implanted.

According to one embodiment, said at least one extending portion extends circumferentially along said equator line, dorsal to the right-left axis of pelvis when being in the defined base position (further disclosed with reference to FIG. 1b).

According to one embodiment, said at least one extending portion extends circumferentially along said equator line, dorsal to the coronal pelvis plane PXY and proximal to the horizontal pelvis PXZ plane when being in the base position.

According to one embodiment, said at least one extending portion extends circumferentially along said equator line, dorsal to the coronal pelvis plane PXY and distal to the horizontal pelvis PXZ plane when being in the base position.

According to one embodiment, one extending portion extends circumferentially along said equator line dorsal to the coronal pelvis plane PXY and proximal to the horizontal pelvis PXZ plane, and one extending portion extends dorsal to the coronal pelvis plane PXY and distal to the horizontal pelvis PXZ plane when being in the base position.

According to one embodiment, said at least one extending portion extends circumferentially along said equator line, in the proximal quadrant of the equator line when being in the base position.

According to one embodiment, said at least one extending portion extends circumferentially along said equator line, in the distal quadrant of the equator line when being in the base position.

According to one embodiment, two extending portions extends circumferentially along said equator line, in the distal and proximal quadrant thereof when being in the base position.

According to one embodiment, said at least one extending portion extends circumferentially along said equator line, in the proximal and dorsal quadrant thereof when being in the base position.

According to one embodiment, said at least one extending portion extends circumferentially along said equator line, in the distal and dorsal quadrant thereof when being in the base position.

According to one embodiment, at least one extending portion extends circumferentially along said equator line, in the distal, dorsal and proximal quadrant thereof when being in the base position.

According to one embodiment, at least a first portion of said medical device is an extending portion, extending beyond said circular equator line, and at least a second portion is a portion not extending beyond said circular equator line, wherein said second portion circumferentially extends along at least ¼ of said circular equator line.

According to one embodiment, at least a first portion of said medical device is an extending portion, extending beyond said circular equator line, and at least a second portion is a portion not extending beyond said circular equator line, wherein said second portion circumferentially extends along at least ⅓ of said circular equator line.

According to one embodiment, at least a first portion of said medical device is an extending portion, extending beyond said circular equator line, and at least a second portion is a portion not extending beyond said circular equator line, wherein said second portion circumferentially extends along at least ½ of said circular equator line.

According to one embodiment, at least a first portion of said medical device is an extending portion, extending beyond said circular equator line, and at least a second portion is a portion not extending beyond said circular equator line, wherein said first portion circumferentially extends along at least ¼ of said circular equator line.

According to one embodiment, at least a first portion of said medical device is an extending portion, extending beyond said circular equator line, and at least a second portion is a portion not extending beyond said circular equator line, wherein said first portion circumferentially extends along at least ⅓ of said circular equator line.

According to one embodiment, at least a first portion of said medical device is an extending portion, extending beyond said circular equator line, and at least a second portion is a portion not extending beyond said circular equator line, wherein said first portion circumferentially extends along at least ½ of said circular equator line.

According to one embodiment, at least a first portion of said medical device is an extending portion, extending beyond said circular equator line, and at least a second portion is a portion not extending beyond said circular equator line, wherein said first portion circumferentially extends along at least 1/10 of said circular equator line.

According to one embodiment, at least a first portion of said medical device is an extending portion, extending beyond said circular equator line, and at least a second portion is a portion not extending beyond said circular equator line, wherein said first portion circumferentially extends along at least 1/10 of said circular equator line, and said second portion circumferentially extends along at least ¼ of said circular equator line.

According to one embodiment, at least two first portions of said medical device are extending portions, extending beyond said circular equator line, and at least a second portion is a portion not extending beyond said circular equator line, wherein said first portions each circumferentially extends along at least 1/10 of said circular equator line, and said second portion circumferentially extends along at least ¼ of said circular equator line.

According to one embodiment, at least two first portions of said medical device are extending portions, extending beyond said circular equator line, and wherein one of said extending portions extends further than the other extending portion.

According to one embodiment, said medical device further comprises two second portions not extending beyond said circular equator line, and wherein said two first extending portion circumferentially extends along said equator line between said two second portions.

According to one embodiment, said medical device further comprises at least one hole, and wherein said at least one hole is adapted to receive a fixating member, for fixating said medical device to the femoral bone.

According to one embodiment, said hole is adapted to receive a screw for fixating said medical device to the femoral bone.

According to one embodiment, said medical device comprises at least one extending portion adapted to clasp the caput femur, or a prosthetic caput femur, for restraining said caput femur, or prosthetic caput femur in said medical device, and wherein said medical device is adapted to release the caput femur or prosthetic caput femur from said medical device when a predetermined strain is placed on said medical device.

According to one embodiment, said extending portion, when implanted, is adapted to be placed such as to restrict the motion range of the hip joint, and wherein said extending portion is adapted to be placed such that adduction is restricted more degrees than flexion.

According to one embodiment, said extending portion, when implanted, is adapted to be placed such as to restrict the motion range of the hip joint, and wherein said extending portion is adapted to be placed such that abduction is restricted more degrees than flexion.

According to one embodiment, said extending portion, when implanted, is adapted to be placed such as to restrict the motion range of the hip joint, and wherein said extending portion is adapted to be placed such that adduction is restricted more degrees than extension.

According to one embodiment, said extending portion, when implanted, is adapted to be placed such as to restrict the motion range of the hip joint, and wherein said extending portion is adapted to be placed such that abduction is restricted more degrees than extension.

The medical device could further comprise a prosthetic replacement for the caput femur, adapted to be received in the bowl shaped inner surface, wherein said prosthetic replacement for the caput femur replacement comprises a spherical portion and an elongated member, adapted to be fixated to the pelvic bone by the elongated member being fixated to said spherical portion of said prosthetic replacement for the caput femur, wherein a) said inner surface comprises an equator line, being the largest circular circumference of said inner contacting surface, being a surface adapted to be in contact with said caput femur, or prosthetic replacement therefore, and b) said at least one extending portion passes beyond said equator line, such that the end portion of said contacting portion of said inner surface forms a circular extension line having a smaller circumference than said equator line, and c) said at least one extending portion circumferentially extends discontinuously along said equator line, such that a portion of said elongated member can be placed between said extension line and said equator line, when said medical device being implanted.

The medical device could comprises a prosthetic replacement for the caput femur having a spherical portion, comprising a spherical portion and an elongated member, adapted to be fixated to the pelvic bone by a connection via the elongated member fixated to said spherical portion of said prosthetic caput femur, wherein:

a) an inner surface comprises an equator line, being the largest circular circumference of said inner surface, b) at least one extending portion passes beyond said equator line, such that the end portion of said contacting portion of said inner surface forms a circular extension line having a smaller circumference than said equator line, and c) said at least one extending portion circumferentially extends discontinuously along said equator line, such that a portion of said elongated member can be placed between said extension line and said equator line, when said medical device being implanted.

The medical device could have at least one of extending portion, when implanted, is adapted to be placed such as to restrict the motion range of the hip joint, and wherein said extending portion is adapted to be placed or shaped such that at least one of adduction, abduction, flexion, extension, a combination of flexion and adduction or abduction, a combination of extension and adduction or abduction, rotation in, rotation out, and any combination of rotation in or out and the other described movements, is restricted more degrees from maximal movement than any of the other.

The at least one extending portion could allow different movement restrictions in different movement directions, wherein said extending portion is constructed according to at least one of the following alternatives; a) circumferentially extending s discontinuously along said equator line having with enough circumferential distance lacking any extending portion and b) extendings with different distal extension in different extending portions or part of such portions of said circumferential extension, in either a orb allowing for different movement restrictions in different movement directions.

The medical device could, comprising a locking member for in situ locking the medical device, wherein: said locking member is adapted to lock said a prosthetic replacement for the caput femur fixated to the pelvic bone, such that the caput femur or prosthetic caput femur remains clasped and restrained in said inner surface, and said locking member is adapted to lock said at least one extension portion, when implanted, having at least the end portion of the extension portion radially fixed within said circular extension line.

The locking member is adapted to lock in at least a first and second locking position.

The locking member is adapted to lock in at least a first and a second locking position, and wherein said locking member is adapted to; in said first locking position, lock a first size caput and/or collum femur, and in said second locking position, lock a second smaller size caput femur and/or collum femur.

A method using a medical device according to any of the preceding medical device claims is further provided, for implantation in a hip joint of a patient, comprising the steps of;

fixating said medical device to the femoral bone of the patient, and wherein said medical device comprises an inner and an outer surface, wherein a contacting portion of said inner surface is bowl shaped and spherical and adapted to face the center of the hip joint, placing the inner bowl shaped surface facing proximally towards the center of the hip joint, and fixating a prosthetic replacement for the caput femur fixated to the pelvic bone having a ball shaped spherical portion receiving said prosthetic replacement for the caput femur inside said inner bowl shaped surface, wherein said medical device comprises at least one extending portion, extending said contacting portion of said inner surface such that said at least one extending portion clasps said spherical portion, clasping said prosthetic replacement for the caput femur, such that said spherical portion is restrained in said bowl shaped inner surface of said medical device.

The inner surface comprises an equator line, being the largest circular circumference of said inner contacting surface, being a surface adapted to be in contact with said caput femur replacement, and said at least one extending portion passes beyond said equator line, such that the end portion of said contacting portion of said inner surface forms a circular extension line having a smaller circumference than said equator line, and said at least one extending portion circumferentially extends discontinuously along said equator line, such that a portion of said elongated member can be placed between said extension line and said equator line, when said medical device being implanted together with the prosthetic replacement for the caput femur, wherein the method comprising the steps of;

wherein the step of placing the inner surface involves the step of placing an inner surface comprising at least one extending portion moving said femoral bone to place said elongated member between said extension line and said equator line.

The method could further comprises the steps of cutting the skin in the hip region dissecting the hip joint implanting the medical device in a hip joint of a patient, fixating a ball shaped replacement of caput femur on the opposite side therefore to the pelvic bone of the patient, fixating a bowl shaped acetabulum replacement on the opposite side and therefore to the femoral bone of the patient, wherein said acetabulum replacement comprises an inner and an outer surface, having a contacting portion of said inner surface being spherical and bowl shaped facing the inner surface to the center of the hip joint having at least one extending portion, extending a contacting portion for contacting the caput femur replacement, placing a caput femur replacement, such that said extending contacting portion of said inner surface is clasping said spherical portion of said caput femur replacement, such that said caput femur replacement is restrained in said bowl shaped inner surface.

The inner surface comprising an equator line being the largest circular circumference of said inner contacting surface, wherein said at least one extending portion is passing beyond said equator line, such that the end portion of said contacting portion of said inner surface forms a circular extension line having a parallel smaller circumference than said equator line, the end portion being the most distal portion of the inner surface being in contact with said caput femur or artificial replacement therefore, placing said said caput femur or artificial replacement therefore symmetrically in said inner surface, and wherein said at least one extending portion is extending circumferentially discontinuously along said equator line, wherein said caput femur replacement is extending into en elongated member, the method involves, placing a portion of said elongated member between said extension line and said equator line when moving said caput femur or artificial replacement therefore in relation to said inner surface.

The at least one extending portion is mounted according to at least one of the following alternatives:

a) extending circumferentially discontinuously along said equator line having enough circumferential distance lacking any extending portion and b) extending with different distal extension in different extending portions or part of such portion of said circumferential extension.

The method could comprise the following steps:
a) cutting the skin in the hip region
b) dissecting the hip joint
c) implanting the medical device M a hip joint of a patient,
d) fixating the artificial replacement of an acetabulum to the femoral bone of the patient, comprising an inner and an outer surface, having a contacting portion of said inner surface being spherical and bowl shaped
e) facing the inner surface to the center of the hip joint having at least one extending portion, extending a contacting portion for contacting the caput femur or a prosthetic replacement therefore,
f) placing a caput femur or an artificial replacement therefore to the pelvic bone having a spherical portion, such that said extending contacting portion of said inner surface is
g) clasping said spherical portion of said caput femur, or an artificial replacement therefore,
h) placing said locking member such that said caput femur, or artificial replacement therefore is restrained in said bowl shaped inner surface, and
i) locking said caput femur or artificial caput femur in said clasped and restrained position in said inner surface, by
j) fixating radially at least the end portion of the at least one extension portion within said circular extension line.

Please note that any embodiment or part of embodiment, feature, method, associated system, part of system described herein or in the associated figures may be combined in any way.

BRIEF DESCRIPTION OF DRAWINGS

The invention is now described, by way of example, with reference to the accompanying drawings, in which:

FIG. 2c shows pelvis in a perspective view from below,
FIG. 2d shows pelvis in a perspective view from below,
FIG. 2e shows the acetabulum, schematically,
FIG. 2f shows the acetabulum, schematically,
FIG. 5 shows the hip joint in section, when a prosthetic replacement for the acetabulum, and a medical device has been implanted,
FIG. 7 shows the pelvic region in a frontal view,
FIG. 8 shows a medical device placed in the femoral bone.

DETAILED DESCRIPTION

Figure 1A:
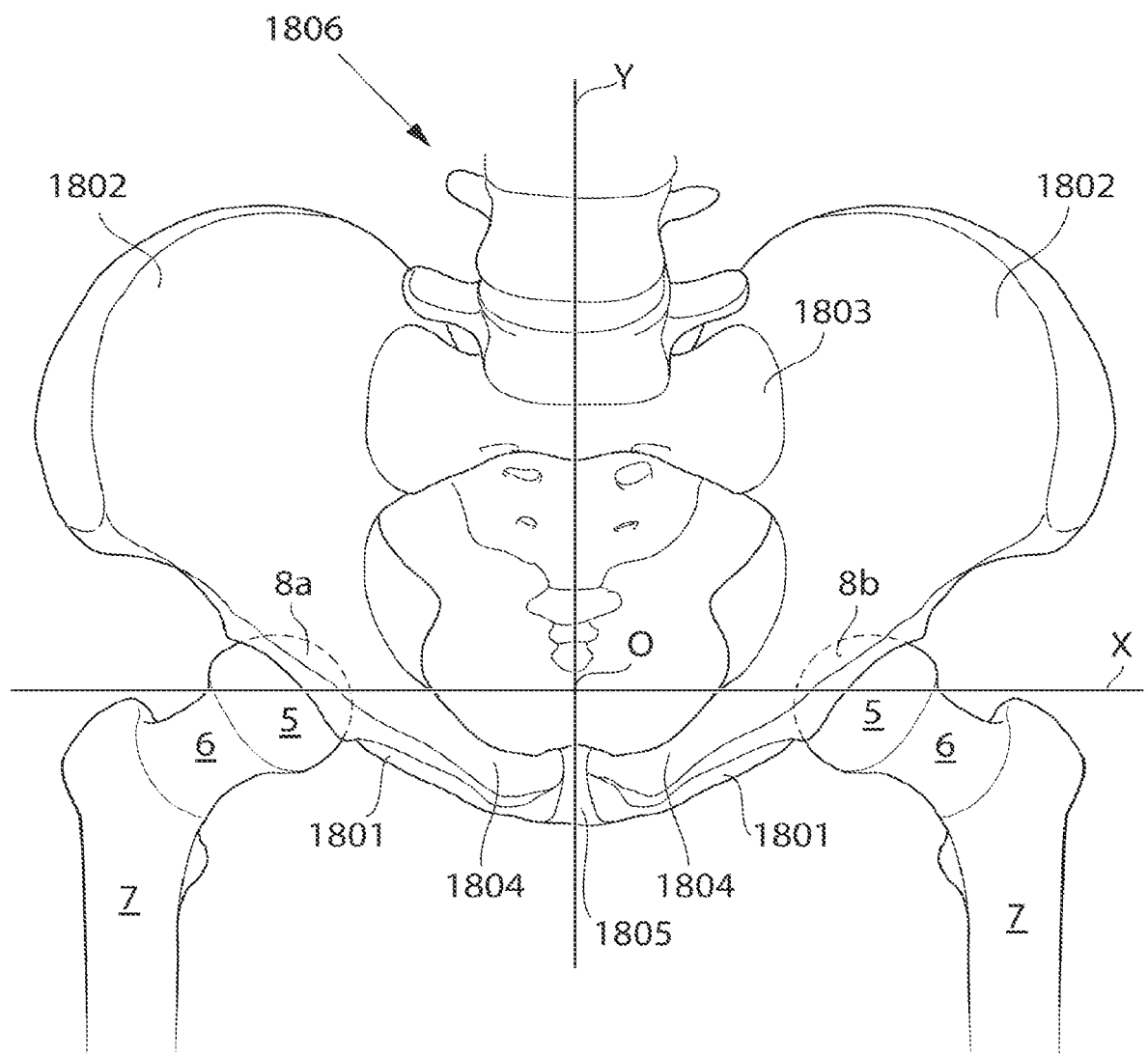
FIG. 1a shows pelvis in a frontal view.

The hip joint is a synovial ball and socket joint which permits a large motion range for allowing a plurality of different movements of the lower limb. Hem a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

When replacing the natural hip joint with a prosthetic hip joint, the depth of the prosthetic acetabulum will affect the motion range, the deeper the acetabulum bowl is made the more restrictive it is to the motion range. A deeper bowl has the advantage of reducing the risk of hip joint luxation, the risk of which is a major drawback with prosthetic hips of today.

The anatomy of the hip joint and its surroundings is further disclosed in Marieb et al., Human Anatomy, 2003, Benjamin Cummings, San Hancisco, pages 195-202 and in Moore et al., Clinically oriented anatomy, 1999, Lippincott, Williams & Wilkins, Baltimore, pages 501-653, both hereby incorporated by reference.

Centrally in the body should herein be understood as a point of reference located at the intersection of the Median plane and the Coronal plane and in the center part of the heart along a longitudinal axis (Caudal-Cranial). Proximal and distal are direction or location terms used in relation to said point centrally in the body and hence a distal point is a point farther away from the central point in relation a proximal point of the same structure. Any plane disclosed herein is to be understood as having infinite extension. Other anatomical terms used herein are further described in Moore et al., Clinically oriented anatomy, 1999, Lippincott Williams & Wilkins, Baltimore, pages 2-10, which is hereby incorporated by reference.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with prosthetic surfaces somewhat different than the functional hip movements of a natural hip joint Everyday activities is to be understood as activities which are not connected to any extreme movements, such that some physical sports require. For example, everyday activities comprise: walking, sitting, cycling etc.

The functional position of an implantable medical device or prosthesis is the position in which the hip joint can perform functional hip movements. The final position is to be understood as a functional position in which the medical device needs no further position change to function.

Arthroscopy is to be understood as key hole surgery performed in a joint since the arthroscopic procedure could be performed in the abdomen of the patient some of the steps of this arthroscopic procedure is mere laparoscopic, however for the purpose of this invention the two terms arthroscopy and laparoscopy is used synonymously and for the purpose of this invention the main purpose of these methods are is that they are minimally invasive.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Elasticity is to be understood as a materials ability to deform in an elastic way.

Stiffness is to be understood as the resistance of an elastic body to deformation by an applied force.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1a shows the pelvis in a frontal view. Pelvis comprises the right and left hip bone making up the pelvic bone, in turn comprising the Sacrum 1803, Ilium 1802, Pubis 1804 and Ischium 1801. The hip joint houses the right and left acetabulum 8a,b placed laterally and distally in the pelvis. The acetabulum 8a,b being a spherically shaped cavity in the hip bones making up one of the parts of the hip joint the acetabulum 8a,b being adapted to house the caput femur 5, being the proximal portion of the femoral bone 7 having a spherical contacting surface adapted to be placed in the acetabulum 8a,b and thus creating the operable hip joint. The pelvis has a right-left axis X extending substantially from the bottom of the left acetabulum 8a to the bottom of the right acetabulum 8b, the pelvis further having a caudal-cranial axis Y extending perpendicular to said right-left axis, centrally and substantially along the length of the patient; passing the dorsal portions of the pubic symphysis 1805 and substantially following the spinal cord 1806, intersecting the left-right axis X.

Figure 1B:
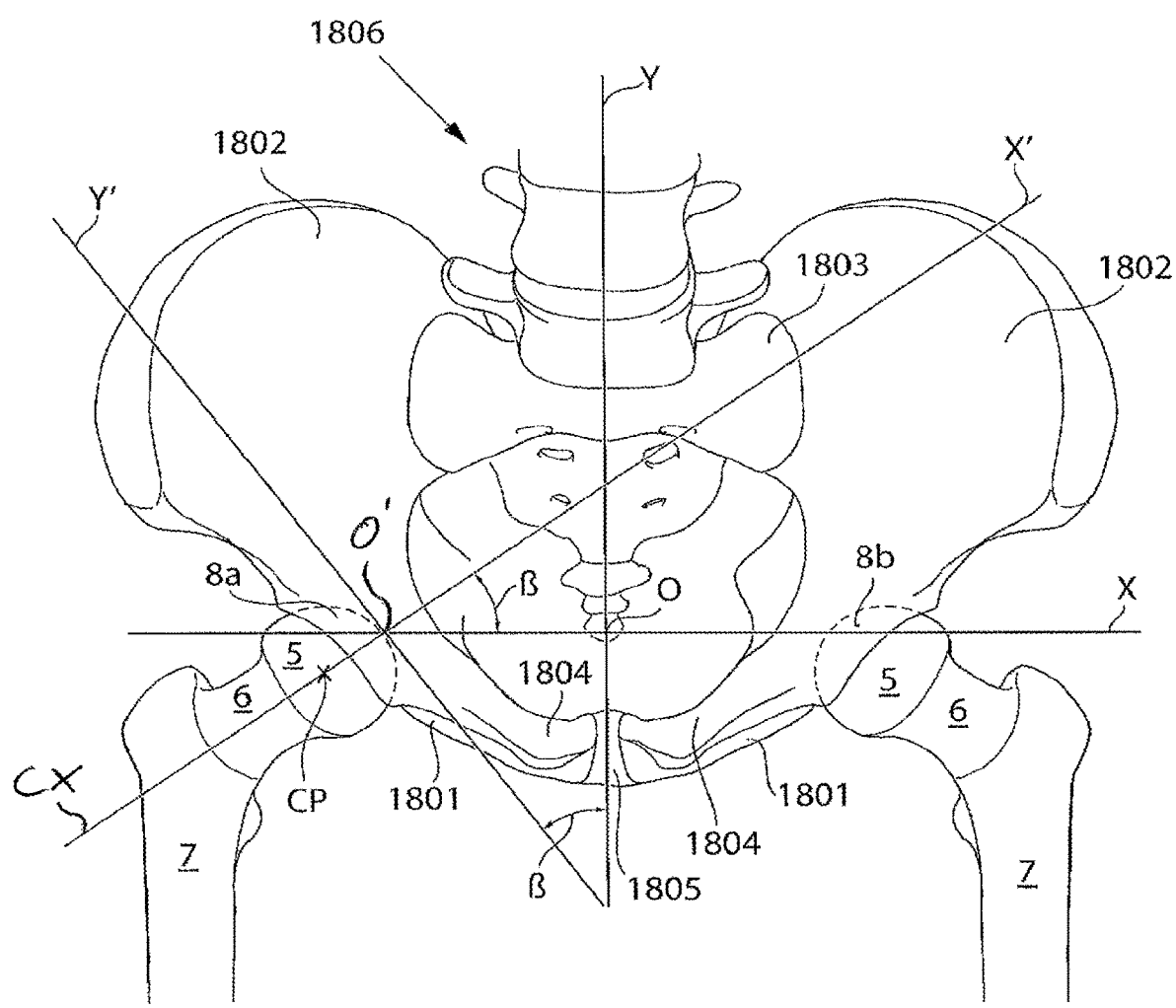
FIG. 1b shows pelvis in a frontal view.

FIG. 1b shows the pelvis in a frontal view disclosing a second, displaced coordinate system. The second displaced coordinate system has its origin O' in the bottom of the acetabulum bowl 8a. The axis X and Y have, in a frontal view, been rotated the angle β, creating the axis X' and Y'. In the defined base position, the acetabulum center axis X' is aligned with the caput and collum femur center axis CX, the caput and collum femur center axis CX is an axis in the extension of the collum and caput femur axis, in the center thereof. The hip joint substantially being in its base position when the patient is standing up or lying down. In said base position, the acetabulum center axis X' goes through a point O' being the origin O' in the bottom of the acetabulum bowl 8a, and a center point CP, being a point in the center of a circle defined by the edges of the acetabulum bowl 8a, and further trough the top of the caput femur 5 and following inside of the collum femur 6, aligned with the collum femur 6. The axis Y' is perpendicular to the axis X' and goes through the origin O' in the bottom of the acetabulum bowl 8a, parallel to a plane defined by the circle defined by the edges of the acetabulum bowl 8a.

Figure 1C:
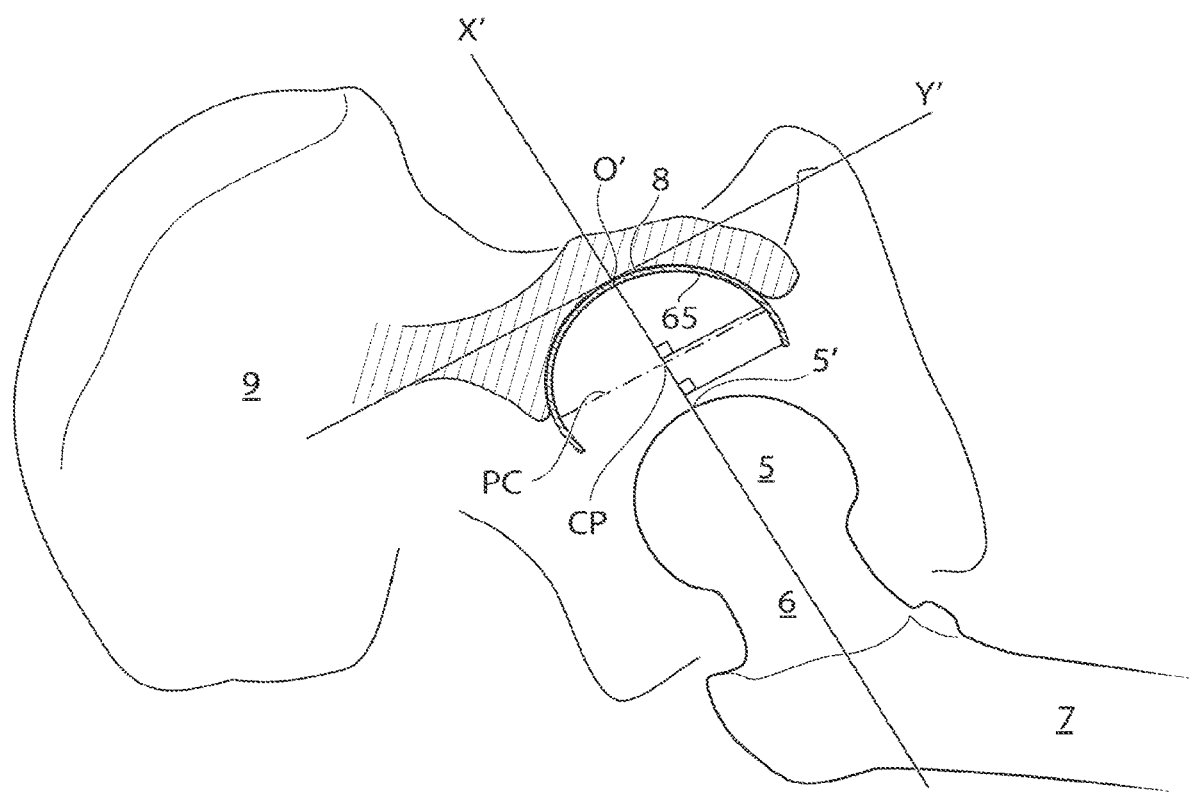
FIG. 1c shows the hip joint in section.

FIG. 1c shows the right pelvic bone 9 in section disclosing the second, displaced coordinate system. The origin O' is in the bottom of the acetabulum bowl 8. The axis X' is aligned with the caput 5 and column 6 femur center axis CX, when the hip joint is in its base position when the patient is standing up or lying down with extended leg. In said base position the axis X' is goes through a point O' being the bottom of the acetabulum bowl 8, and a center point CP, being a point in the center of a circle defined by the edges of the acetabulum bowl 8, and further through the top of the caput femur 5' and following inside of the collum femur 6, aligned with the column femur 6. The axis Y' is perpendicular to the axis X', goes through the origin O' in the bottom of the acetabulum bowl 8, parallel to the plane PC defined by the circle defined by the edges of the acetabulum bowl 8.

Figure 2A:
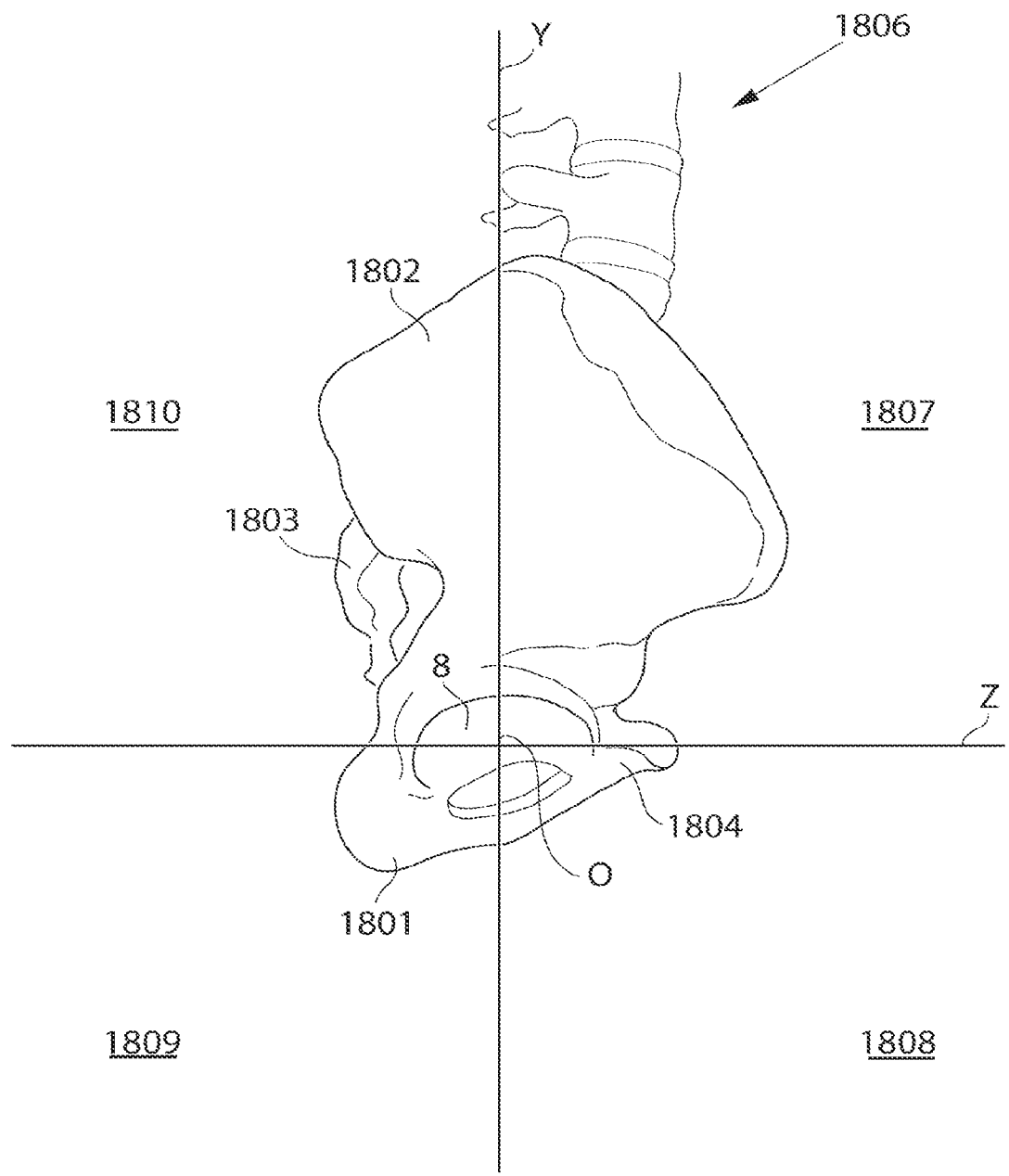
FIG. 2a shows pelvis in a lateral view.

FIG. 2a shows the pelvis in a lateral view, thus displaying the posterior side of Ilium 1802, the anterior side of Ichum 1801, the anterior side of Pubis 1804, and Sacrum 1803 in a lateral view. The pelvis has furthermore a dorso ventral axis Z being perpendicular to the caudal-cranial axis Y and the right, left axis X shown in FIG. 1, and intersecting them both creating a common origin O for the three axis X,Y,Z. The dorso ventral axis Z and the caudal-cranial axis Y thus being oriented such that a horizontal pelvis plane PXZ extends from the dorso ventral axis Z, and a coronal plane PXY extends from the caudal-cranial axis Y.

Figure 2B:
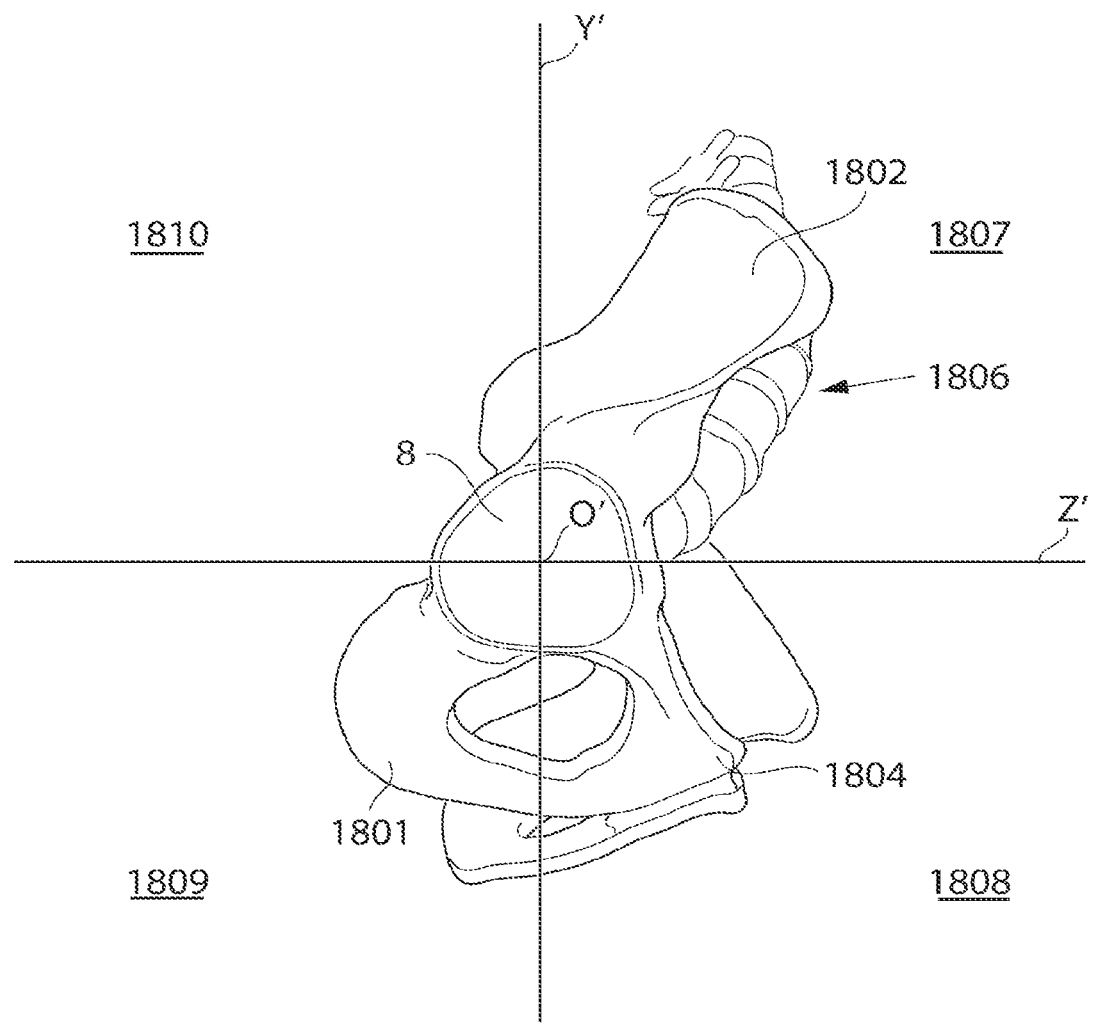
FIG. 2b shows pelvis in a lateral view.

FIG. 2b shows the pelvis in a plane view from the side and slightly from below, in the direction of the axis X' (further disclosed with reference to FIGS. 1b and 1c). The view of FIG. 2b displaying the axis Y' and Z' with origin O' in the bottom of the acetabulum bowl 8 making up the acetabulum coordinate system. The axis Y', Z', in this plane view, dividing the acetabulum bowl 8 into four quadrants: the proximal-frontal quadrant 1807, the distal-frontal quadrant 1808, the distal-dorsal quadrant 1809 and the proximal-dorsal quadrant 1810.

FIG. 2c shows the pelvis in a perspective view from below and slightly from the front, displaying the right-left axis X passing through the center of the right and left acetabulum 8. The right-left axis X is perpendicular to the dorso ventral axis Z which also is perpendicular to the caudal-cranial axis Y. The coronal plane PXY extends from the dorso ventral axis Y, and the horizontal pelvis plane PXZ extends from the dorso ventral axis Z, thus being perpendicular to the coronal plane PXY.

FIG. 2d shows the coordinate system X,Y,Z and planes PXY, PXZ of FIG. 2c, and the second, displaced, coordinate system X', Y', Z' being the coordinate system of the acetabulum 8, also shown in FIG. 2b. The axis of the coordinate system of the acetabulum X', Y', Z' having their origin O' in the bottom of the acetabulum bowl 8, the axis X' being aligned with the caput and collum center axis. FIG. 2d further discloses the vertical acetabulum plane PX'Y' and the horizontal acetabulum plane PX'Z', PX'Y' being defined by the axis X',Y' and the vertical acetabulum plane PX'Z' being defined by the axis X',Z'. The planes PX'Y' and PX'Z' dividing the acetabulum bowl 8 into four quadrants, the proximal-frontal quadrant 1807, the distal-frontal quadrant 1808, the distal-dorsal quadrant 1809 and the proximal-dorsal quadrant 1810, in accordance with what is previously disclosed, with reference to FIG. 2b. FIG. 2d further shows the location of foramen obturatum 1871.

FIG. 2e shows, schematically how the acetabulum coordinate system X',Y',Z' relates to the hemisphere defined by the acetabulum bowl 8.

FIG. 2f shows, schematically, how the vertical acetabulum plane PX'Y', and the horizontal acetabulum plane PX'Z' divides the acetabulum 8 into four quadrants; the proximal-frontal quadrant 1807, the distal-frontal quadrant 1808, the distal-dorsal quadrant 1809 and the proximal-dorsal quadrant 1810, in accordance with the previously disclosed, with reference to FIGS. 2b and 2d.

Figure 2G:
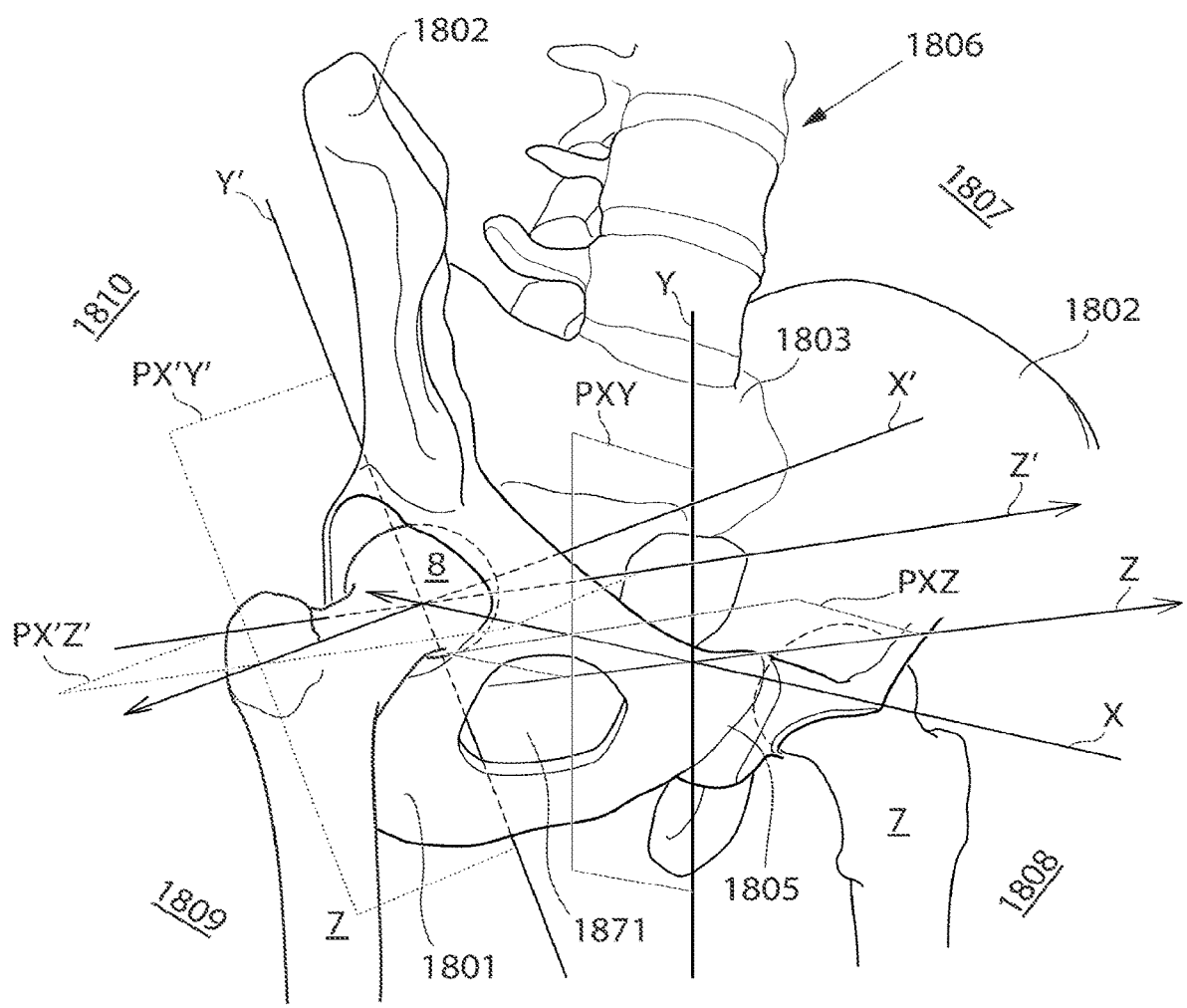
FIG. 2g shows pelvis in a perspective view from below.

FIG. 2g shows the view of FIG. 2d, and in addition it shows the horizontal and vertical acetabulum planes P'Y' and PX'Z' also being the caput and collum femur horizontal and vertical planes PX'Y' and PX'Z', analogically dividing the caput and collum femur into four quadrants.

Figure 3:
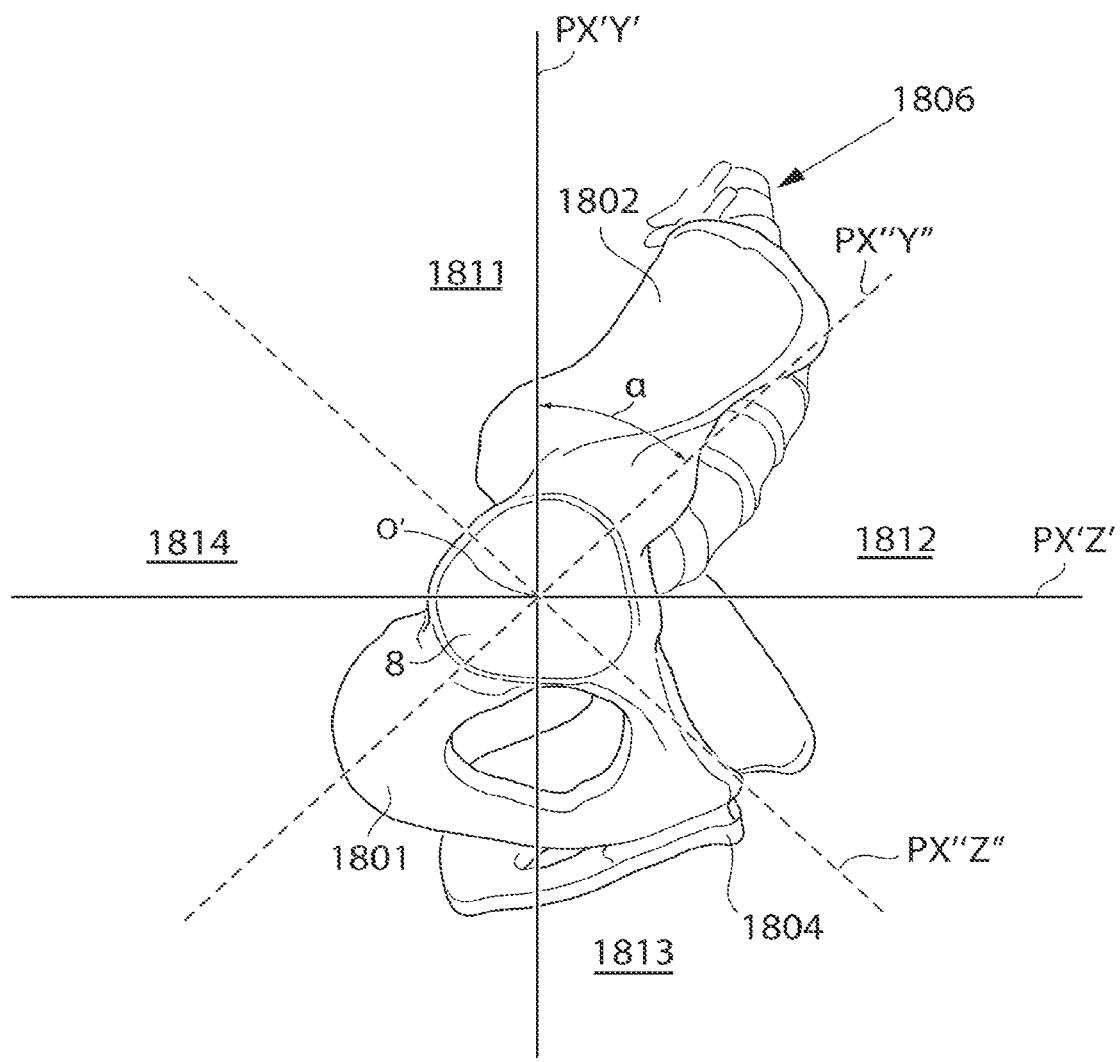
FIG. 3 shows pelvis in a lateral view.

FIG. 3 shows pelvis in the same view as FIG. 2b. Here the vertical and horizontal acetabulum planes PX'Y' and PX'Z' (further disclosed with reference to FIG. 2d) are shown in a strict plane view. Two further planes PX'Y' is introduced in FIG. 3, which planes are rotated an angle α of 45° clockwise. The planes PX'Y' and PX'Z', analogous to the planes PX'Y' and PX'Z', divides the acetabulum bowl into four different quadrants, being a proximal quadrant 1811, a frontal quadrant 1812, a distal quadrant 1813 and a dorsal quadrant 1814.

Figure 4:
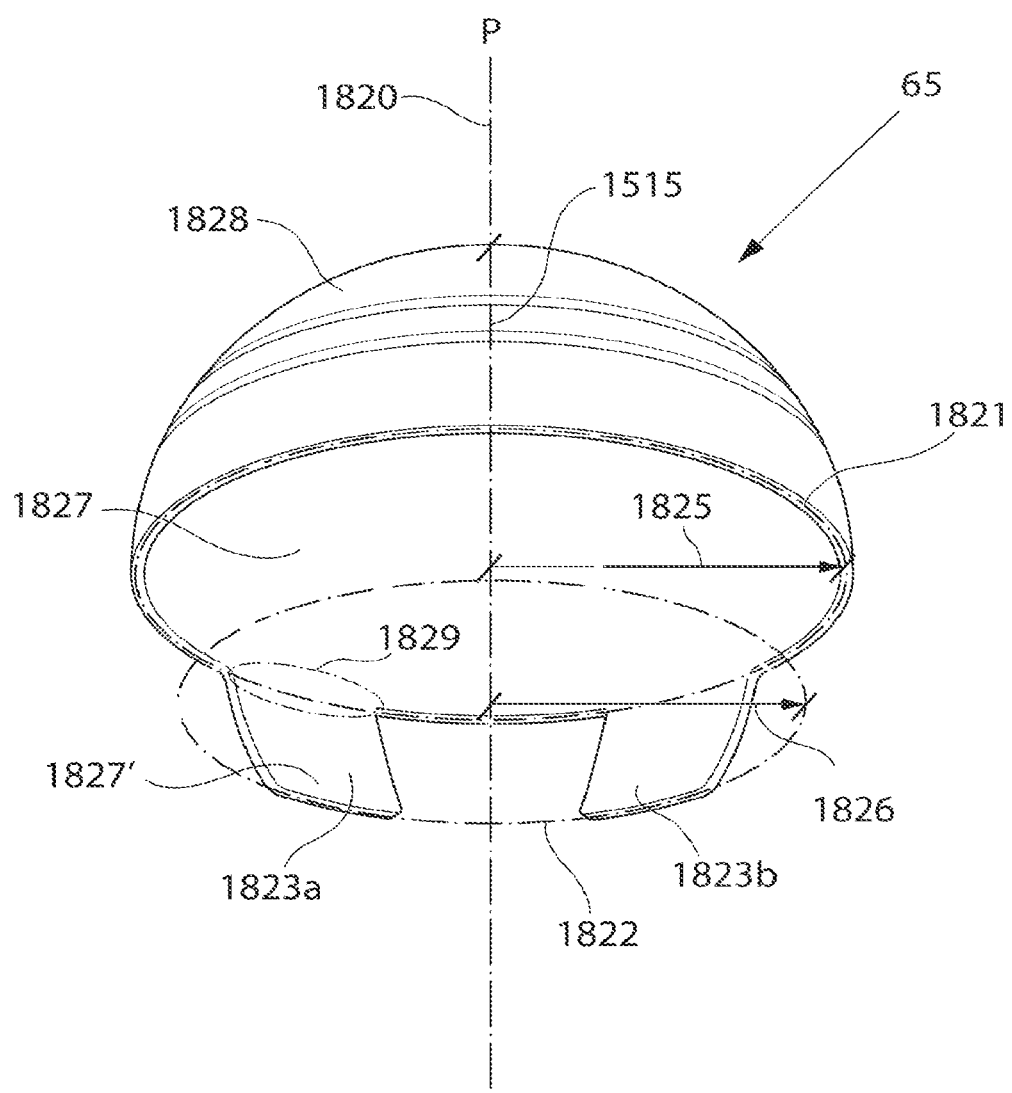
FIG. 4 shows a prosthetic replacement for the acetabulum, according to one embodiment.

FIG. 4 shows a medical device for implantation in a hip joint of a patient the medical device is adapted to be fixated to the femoral bone of the patient in an opposite embodiment for example by means of an adhesive, such as bone cement, or mechanical fixating members, such as orthopedic screws. The medical device comprises an inner 1827 and an outer 1828 surface. A contacting portion of the inner surface 1827 is spherical and faces the center of the hip joint, when the medical device is implanted. The inside of the medical device is adapted to receive a prosthetic replacement for a caput femur adapted to be fixated to the pelvic bone having a spherical portion, and the spherical contacting portion of the inner surface 1827 is adapted to be in contact with a spherical portion of the outer surface of the prosthetic replacement of the caput femur. The medical device, comprises two extending portions 1823a,b, extending the contacting portion of the inner surface 1827' such that the extending portions 1823a,b clasps the spherical portion of a prosthetic replacement of a caput femur, for restraining the spherical portion in the medical device. The medical device is adapted to receive the prosthetic spherical portion, fixated to the pelvic bone, connected via a prosthetic elongated portion. The inner surface 1827 comprises an equator line 1821, being the largest circular circumference of the inner surface. The two extending portions passes beyond the equator line 1821, such that an end portion 1829 of the contacting portion, here being of the extending portion 1823b of the inner surface 1827, forms a circular extension line 1822 placed proximal to the equator line 1821, when the medical device is implanted, and having a smaller circumference than the equator line 1821; thus a distance 1826 between a center axis P of the medical device and the extension line 1822 is shorter than a distance 1825 between the center axis P and the equator line 1821.

FIG. 5 shows the medical device described with reference to FIG. 4 when implanted. According to this embodiment the medical device is adapted to be fixated using orthopedic screws 1830, mechanically fixating the medical device to the femoral bone 5, by the medical device comprising holes through which the screws 1830 are placed. In FIG. 5 the contacting portion of the inner surface 1827 has been placed in contact with the prosthetic spherical portion being connected to a the prosthetic elongated portion 2201, the prosthetic spherical 45 and elongated portions 2201 replacing the proximal portion of the femoral bone. The two extending portions 1823*a* and 1823*b* extending the contacting portion of the inner surface and clasping the spherical portion 45, for restraining the spherical portion in the medical device. The inner surface comprising the equator line 1821, and the extending portions 1823*a,b* passing beyond the equator line 1821 and comprising the more proximal extension line 1822 having a smaller circumference than the equator line 1821. The more proximal extension line 1822 being placed at a distance D1 from the equator line 1821. According to this embodiment the extension line 1822 is parallel to the equator line 1821, however this is not necessarily so in other embodiments. The extension portion 1823*a* according to the embodiment shown in FIG. 5 extends circumferentially along the equator line, a distance D2. Along another portion of the equator line, a distance D3, there are no extending portion, which enables the elongated portion 2201 to enter the space between the first and second extending portions 1823*a,b* which creates a larger movement range of the hip joint for further increase of the movement range, the recess 2203 in the elongated portion 2201 is adapted for some section of the extending portion to enter the recess 2203.

The extending portion, according to any of the embodiments, adapted to clasp the prosthetic spherical portion, for restraining to the prosthetic acetabulum 65, could further be adapted to release the prosthetic spherical portion 45 when a large enough strain is placed on the joint. This feature enables the prosthetic spherical portion to be fixedly attached in the prosthetic acetabulum 65 in normal use, and be released from the prosthetic acetabulum, e.g. in case of an accident, thus reducing the risk of damaging the bodily structures, such as the femoral bone, or the fixations between bodily structures and prosthetic parts.

Figure 6A:
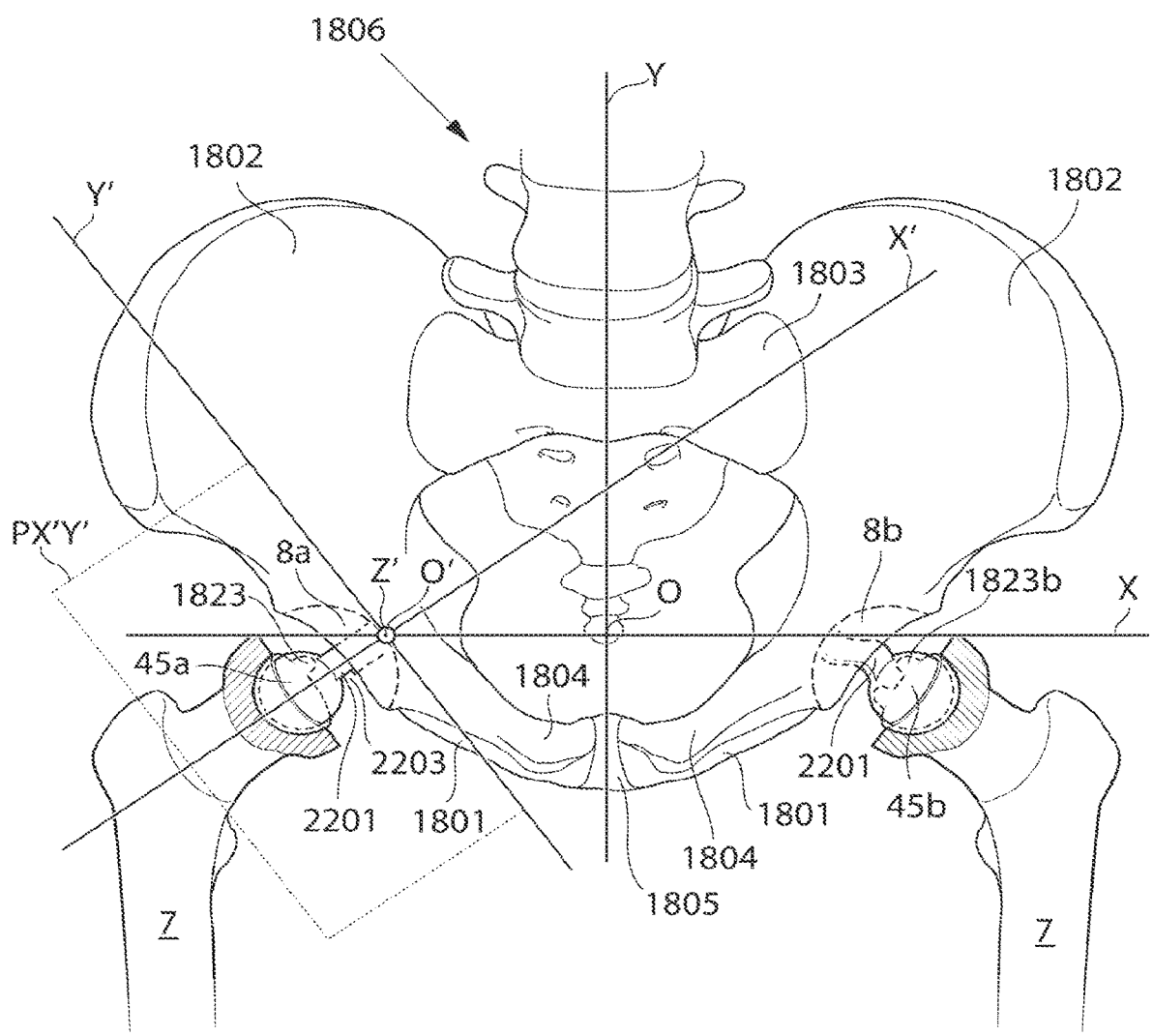
FIG. 6a shows the pelvic region in a frontal view.

According to one embodiment, the extending elements are placed such that the extending elements restricts the motion range minimally, or in ways which are not limiting the motion range used in everyday life. This is enabled through the placing of the extending portions, or the interaction between the extending portion and adaptations of the prosthetic elongated portion. The hip joint is a synovial ball and socket joint which permits a large motion range for allowing a plurality of different movements of the lower limb. From a neutral position, the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed. In the movement ranges of abduction and adduction the depth of the acetabulum bowl and thus the extending portions does not restrict the motion range in a critical way since the motion range of the normal hip is restricted in these movements, in normally agile persons, by the muscles, tenors and ligaments surrounding the hip joint FIG. 6*a* shows a frontal view of pubis and the proximal portions of the femoral bones 7 when two embodiments prosthetic replacement for the acetabulum 65 has been implanted in the hip joint. The prosthetic replacements for the acetabulum shown comprises one extending portion 1823, here placed dorsal to the vertical acetabulum plane PX'Y' in the base position, thus only partially limiting abduction in far excess of 50°. According to the embodiment shown, the extending portion 1823 extends circumferentially along the equator line 1821 about 1/10 of the length of the equator line 1821, however in other embodiments the extending portion 1823 extends along as much as half of the length of the equator line 1821, and in other embodiments the extending portion 1823 extends as little as about 1/30 of the length of the equator line 1821. The prosthetic replacement for the acetabulum placed in the left femoral bone comprises two extending portions 1823*a,b*, both being placed dorsal the corresponding vertical acetabulum plane PX'Y' of the left acetabulum (not shown) in the base position, thus limiting the motion range of the hip joint in a non restrictive way, in relation t everyday activities. In both the right and left embodiment the extending portions 1823 extends discontinuously along the equator line 1821 thus enabling the elongated portion 2201 to partially be placed between the equator line and the extension line, and in the left embodiment, be placed between the extending portions 1823*a,b* thus entering the cavity between the extending portions 1823*a,b*. The recess 2203 of the prosthetic elongated portion 2201 implanted in the right hip joint is radially placed, in relation to the caput and collum center axis, such that the a section of the prosthetic elongated portion 2201, can enter the recess for further increasing the movement range of the prosthetic acetabulum surface 65 in relation to the elongated 2201 and spherical 45*a* portion. The curving of the prosthetic elongated portion 2201 implanted in the left hip joint is radially placed, in relation to the caput and collum center axis, for further increasing the movement range of the prosthetic acetabulum surface 65 in relation to the elongated 2201 and spherical 45*b* portion.

Figure 6B:
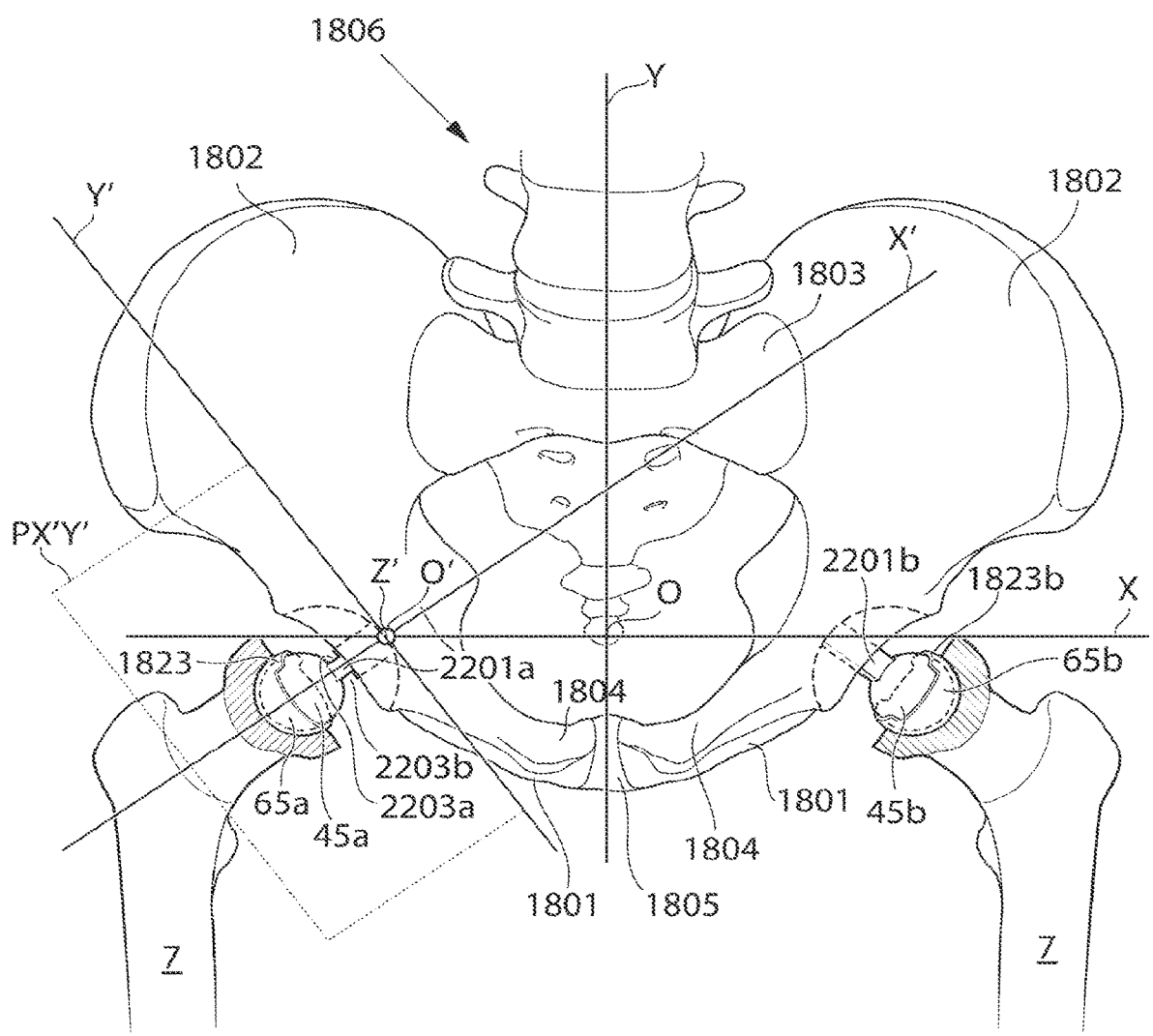
FIG. 6b shows the pelvic region in a frontal view.

FIG. 6*b* shows a frontal view of pubis and the proximal portions of the femoral bones 7, when two further embodiments of the prosthetic replacements have been implanted. The embodiment shown placed on the right side is an embodiment in which the prosthetic elongated portion 2201*a* comprises a first 2203*a* and second 2203*b* recess placed at the restricting portion of the elongated portion 2201*a*. The prosthetic elongated portion 2201 is connected to a prosthetic spherical portion 45*a* which is restrained in a prosthetic replacement for the acetabulum 65*a* fixated to the femoral bone. The prosthetic replacement for the acetabulum 65*a* comprises extending portions 1823 clasping the prosthetic spherical portion 45*a* and thus restraining the spherical portion in the prosthetic replacement for the acetabulum 65*a*. The extending portions 1823 is placed in the proximal quadrant in the base position, thus limiting the motion range of the hip joint in a non restrictive way, in relation to everyday activities. According to the embodiment shown, the extending portion 1823 extends circumferentially along the equator line 1821 about 1/10 of the length of the equator line 1821, however in other embodiments the extending portion 1823 extends along as much as half of the length of the equator line 1821, and in other embodiments the extending portion 1823 extends as little as about 1/30 of the length of the equator line 1821. The prosthetic elongated portion 2201*b* shown placed in the left hip joint comprises a narrow portion connected to the prosthetic spherical portion 45*b*. The narrow portion enables a relatively large motion range in relation to the elongated portion even though the prosthetic replacement for the acetabulum comprises extending portions 1823*a,b* extending beyond the equator line of the prosthetic spherical portion 45*b*, thus clasping the spherical portion and restraining it in a fixated position.

FIG. 7 shows the pelvis and the proximal portions of the femoral bones 7 including the embodiment of FIG. 25*a*, with the difference that the natural caput femur has been replaced by a prosthetic replacement for the acetabulum the prosthetic elongated portion 2201 is here coordinated with the extending portions 1823 of the prosthetic replacement for the acetabulum 65a,b for further improving the motion range of the hip joint, or not limiting the natural motion range of the hip joint.

FIG. 8 shows the medical device according to an embodiment in which the medical device comprises two extending portions 1823a,b. The medical device is placed on a prosthetic elongated portion 2201, to which a prosthetic spherical portion 45 is attached. The prosthetic elongated member 2201 is here adapted ti further improve the motion range of the hip joint or not limiting the natural motion range of the hip joint; by the prosthetic elongated portion 2201 comprising a recess 2203 in which the extending portions 1823 can enter.

Figure 9:
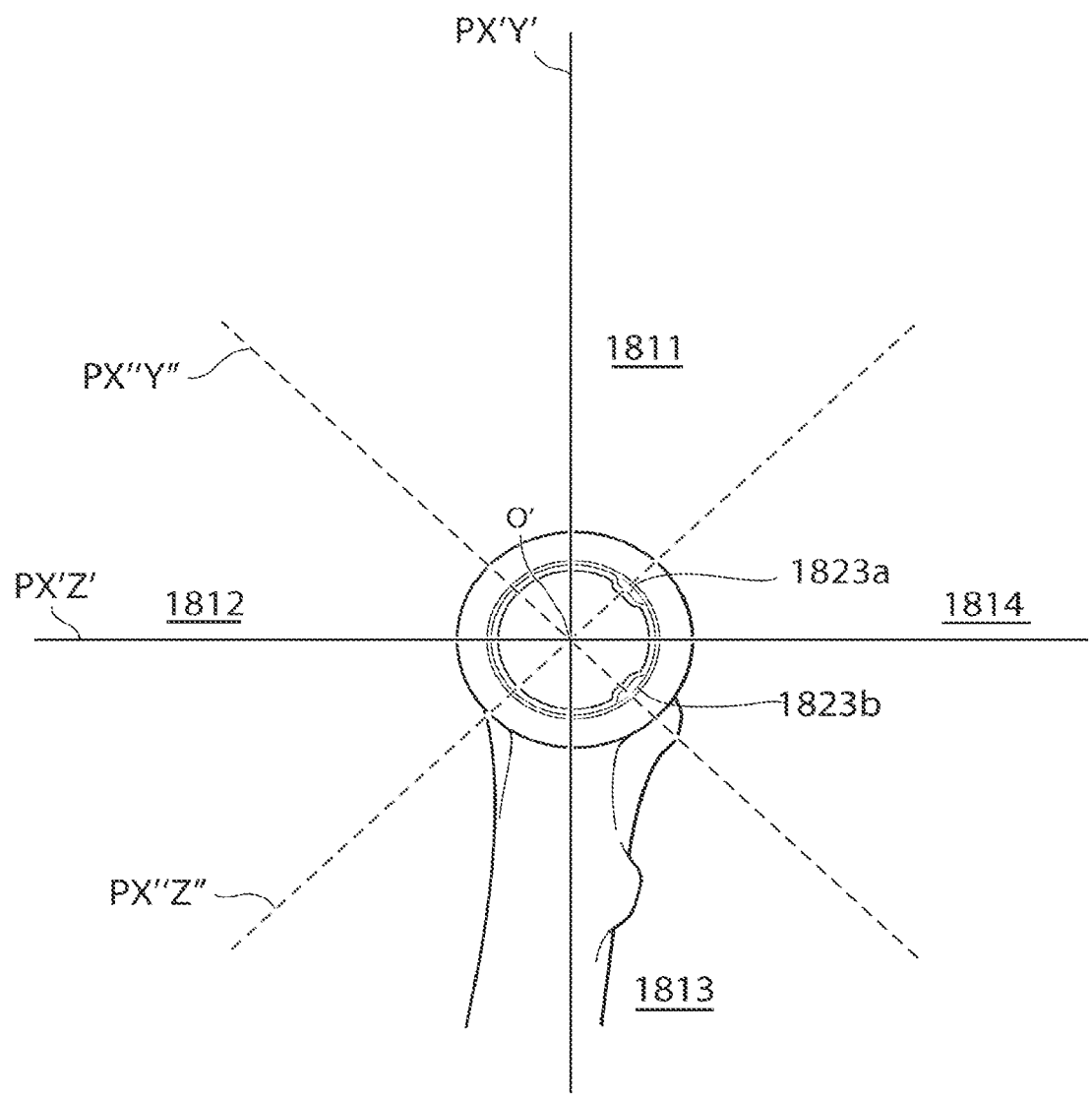
FIG. 9 shows the femoral bone in a lateral view.

FIG. 9 shows the pelvis in a lateral view, the prosthetic replacement for the acetabulum 65 in the femoral bone comprises two extending portions 1823a,b, both extending circumferentially along the equator line (as disclosed in for example FIG. 5) dorsal to the caudal-cranial axis Y when being in the base position and being adapted to clasp the caput femur or a prosthetic replacement therefor. The extending portions 1823a,b extending dorsal to the caudal-cranial axis Y when being in the base position and thus reducing the limiting effect tat the extending portions 1823a, b, have on the motion range of the hip joint. According to the embodiment shown in FIG. 9 the extending portion 1823a, placed proximally in the acetabulum, extends circumferentially a distance of about ¼ of the length of the equator line, and the extending portion 1823b, placed distally in the acetabulum when being in the base position, extends circumferentially a distance of about ⅒ of the length of the equator line, however it is equally conceivable that this relationship is the other way around, or that any of the extending portions circumferentially extends a distance of as much as half of the length of the equator line, thus extending the entire distance of the equator line being dorsal to the vertical acetabulum plane PXY, or that any of the extending portions 1823a,b extends a distance being as little as ⅟₃₀ of the distance of the equator line. According to the embodiment shown in FIG. 9, the first extending portion 1823a extends in distal-lateral direction from the acetabulum, and the second extending portion 1823b extends medially towards foramen obturatum when being in the base position.

Figure 10:
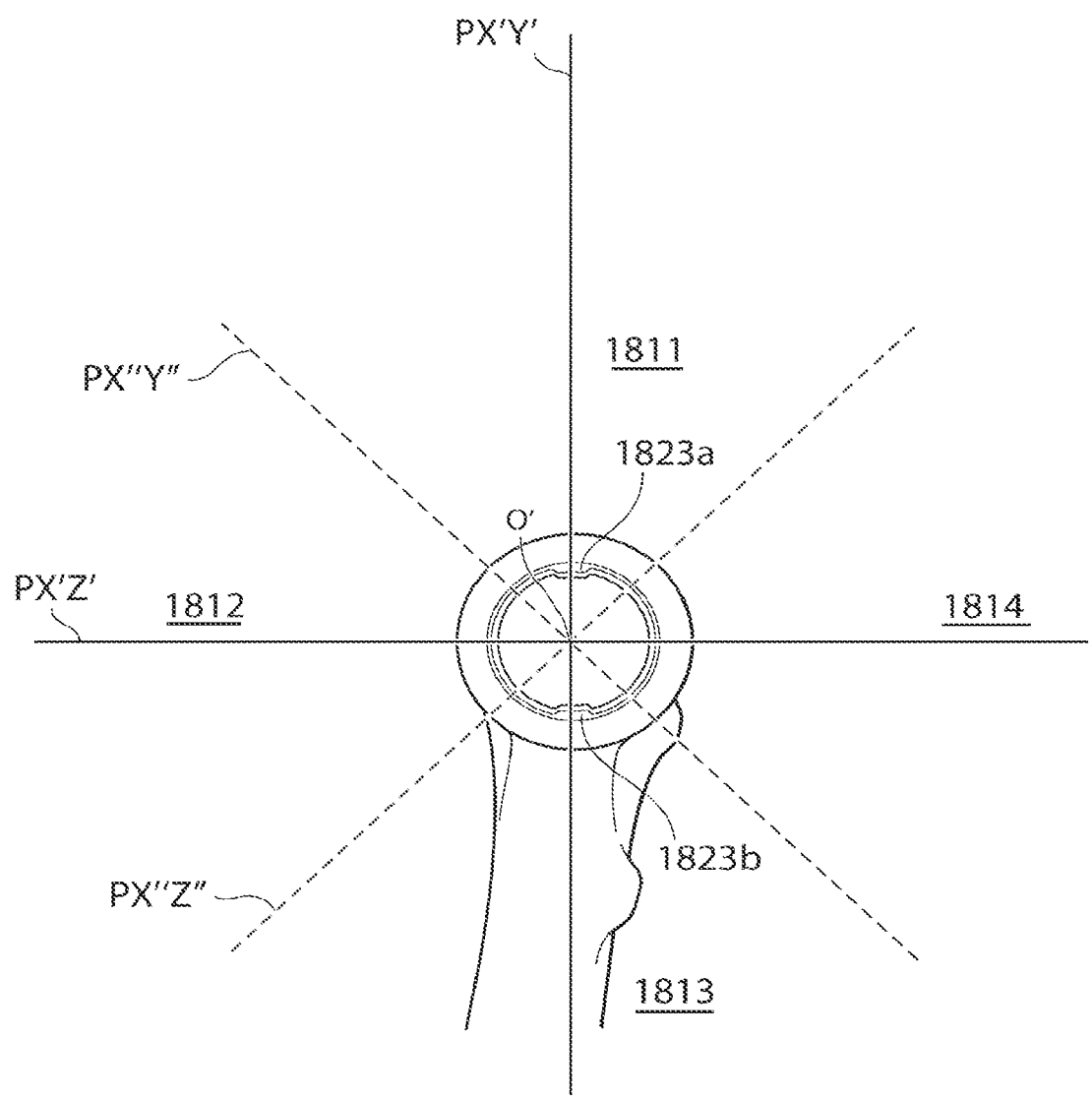
FIG. 10 shows the femoral bone in a lateral view.

FIG. 10 shows the pelvis in a lateral view, the prosthetic replacement for the acetabulum 65 in the femoral bone comprises two extending portions 1823a,b, the two extending portions 1823a,b extends in the proximal quadrant 1811 and the distal quadrant 1813 when being in the base position, respectively.

There are multiple ways in which the extending portions 1823 can be adapted to reduce the effects that the extensions have on the motion range of the hip joint.

Figure 11:
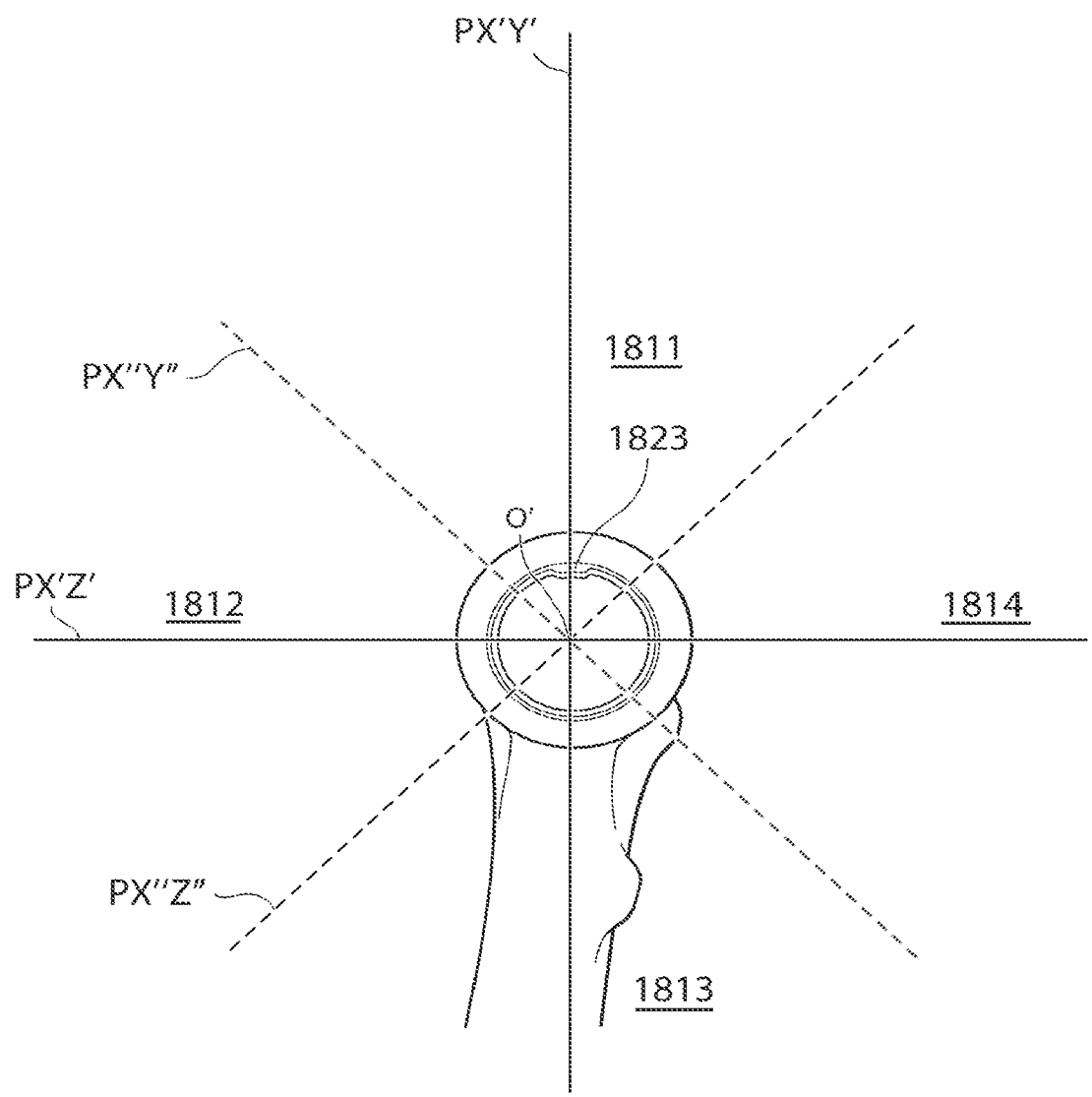
FIG. 11 shows the femoral bone in a lateral view.

FIG. 11 shows the pelvis in a lateral view, the prosthetic replacement for the acetabulum 65 in the femoral bone shown comprises one extending portion 1823 extending and being adapted to clasp the caput femur, or a prosthetic replacement therefor. The extending portion 1823 extends circumferential along the equator line within the proximal quadrant 1811 when being in the base position, which is further disclosed with reference to FIG. 3. According to the embodiment shown in FIG. 4, the extending portion 1823 extends in distal-lateral direction from the acetabulum when being in the base position.

Figure 12:
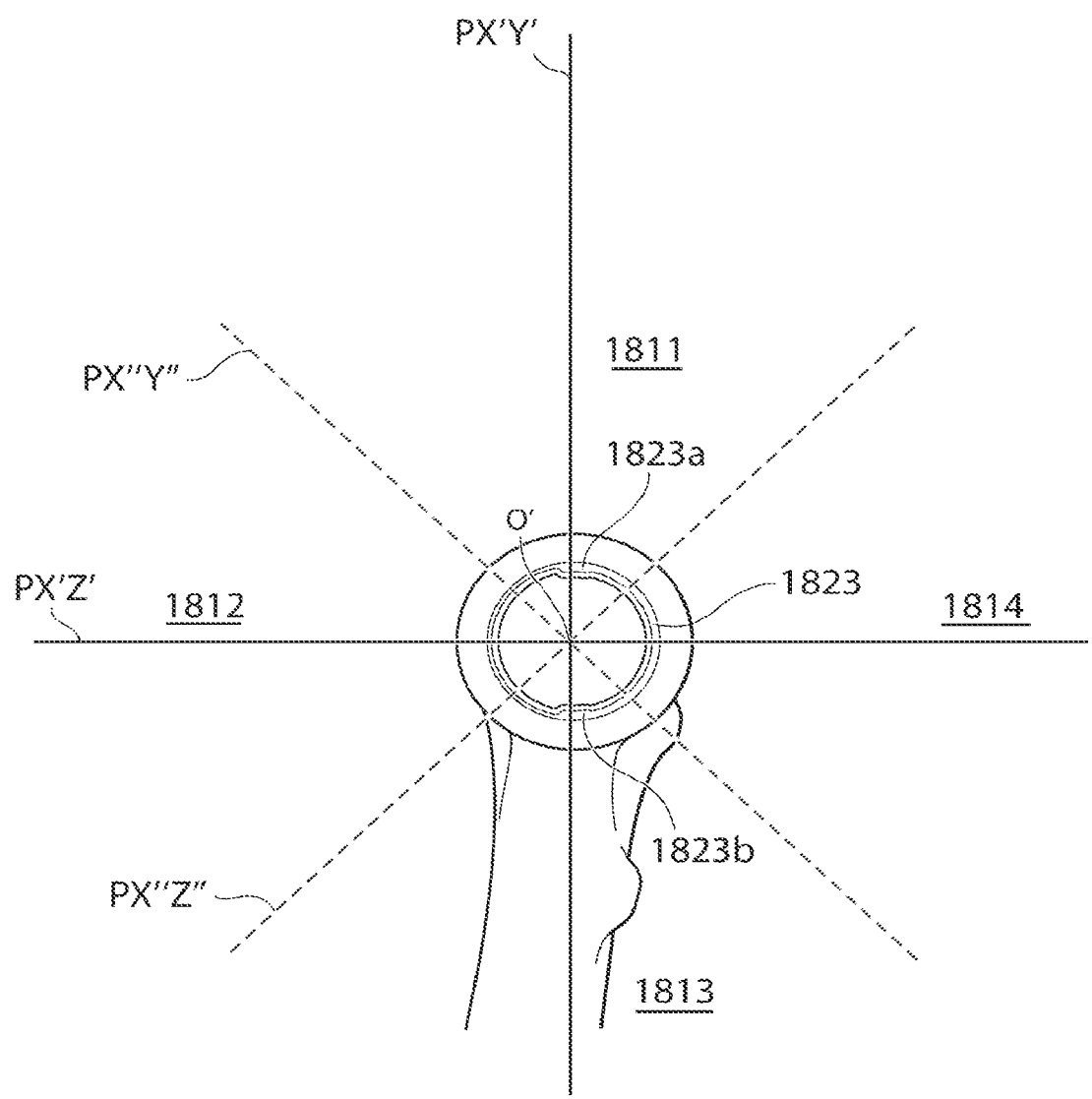
FIG. 12 shows the femoral bone in a lateral view.

FIG. 12 shows the pelvis in a lateral view, the prosthetic replacement for the acetabulum 65 in the femoral bone shown comprises a continuously extending portion 1823 with two extending portions 1823a and 1823b extending further in relation to the average extension of the extending portion. The entire extending portion is placed in the proximal, distal and dorsal quadrants and the extending portions 1823a,b extending further than the average extension of the extending portion 1823 extends in the proximal and distal quadrant when being in the base position.

Figure 13:
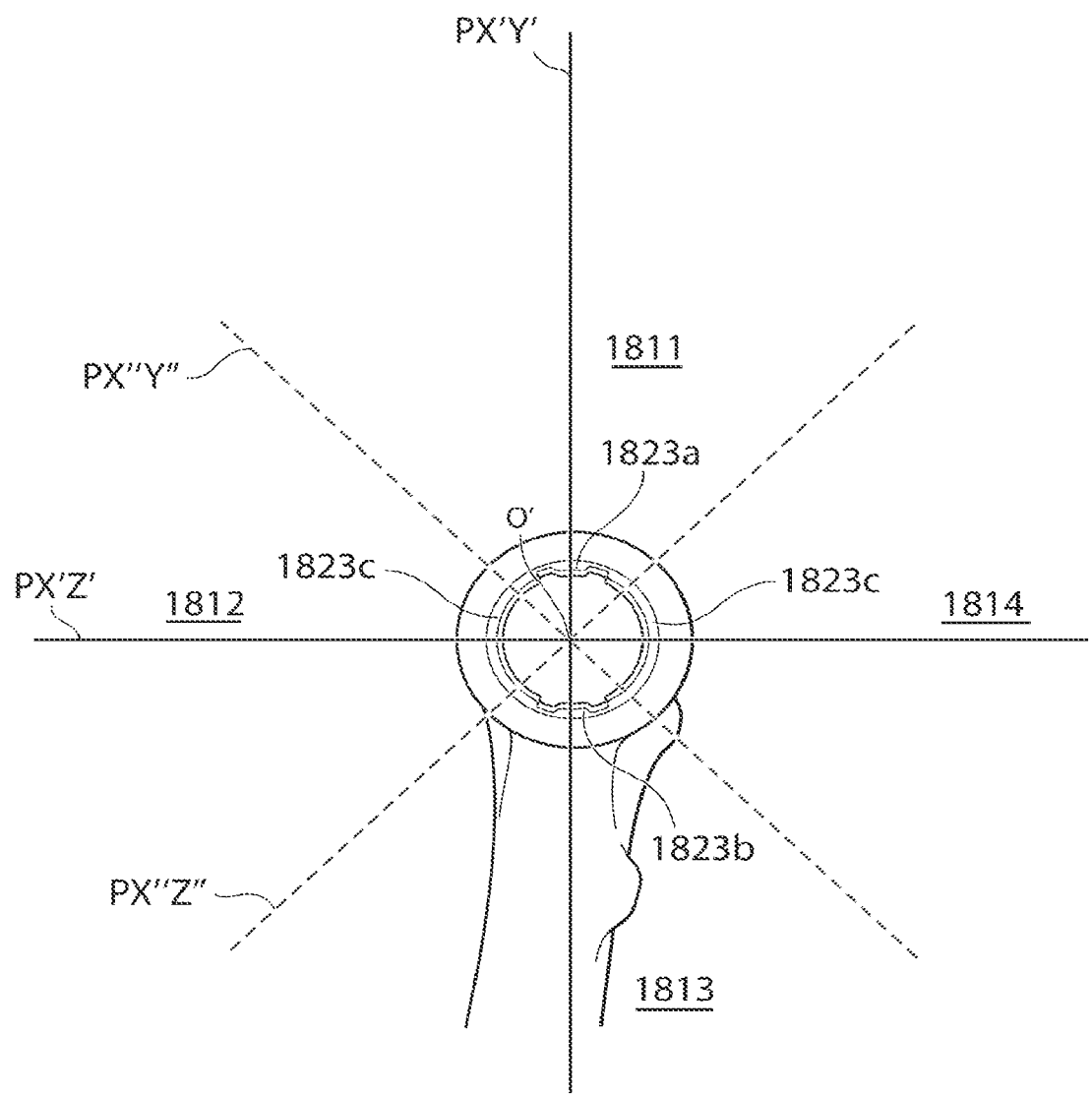
FIG. 13 shows the femoral bone in a lateral view.

FIG. 13 shows the pelvis in a lateral view, the prosthetic replacement for the acetabulum 65 in the femoral bone shown comprises four extending portions 1823a,b,c,d, wherein the first 1823a and second 1823b extending portions extends in the proximal and distal quadrant; respectively, thus the first extending portion 1823a extending in distal-lateral direction from the acetabulum, and the second extending portion 1823b extending medially towards foramen obturatum when being in the base position. The third extending portion 1823c when being in the base position extending in the frontal quadrant 1812, out from the acetabulum in dorsal direction, extends less than the first and second extending portion, since extending portions 1823c in the frontal quadrant is more limiting to the normal motion range of the hip joint. The fourth extending portion 1823d extends in the dorsal quadrant in accordance with the third extending portion 1823c do not extend as far as the first and second extending portions when being in the base position.

Figure 14:
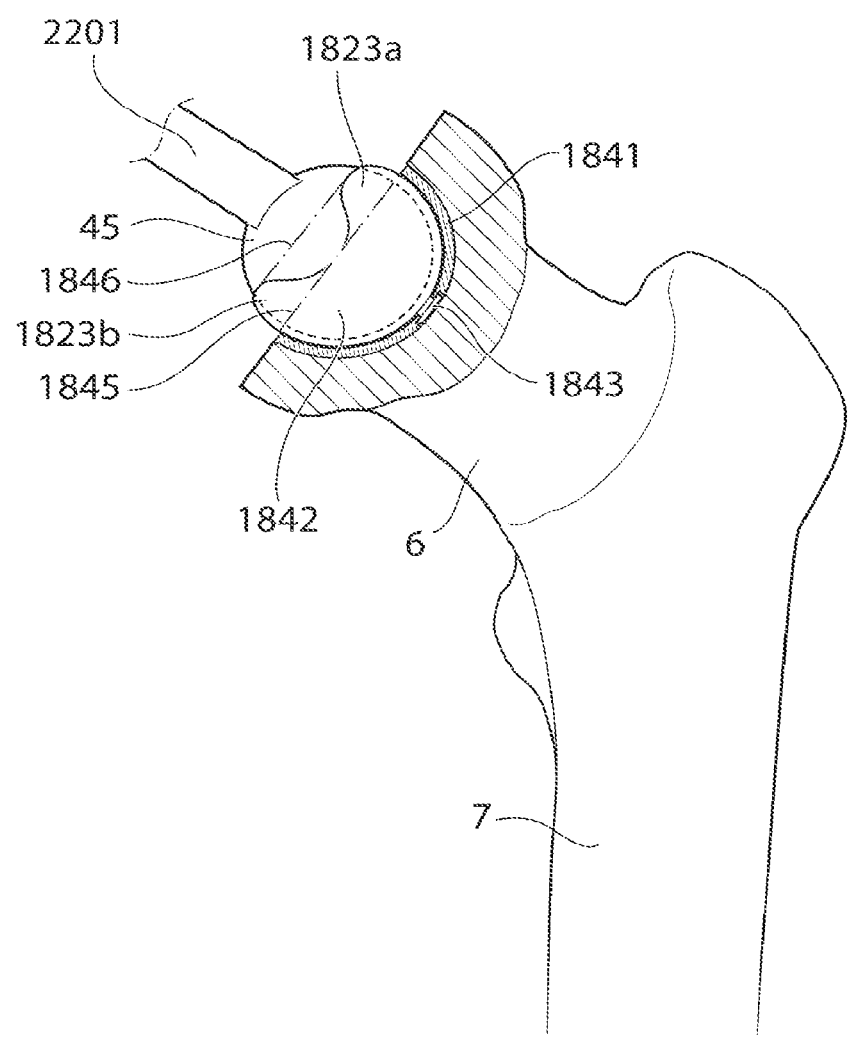
FIG. 14 shows a medical device placed in the femoral bone.

FIG. 14 shows an alternative embodiment of the prosthetic replacement for the acetabulum 65. In the alternative embodiment the prosthetic replacement for the acetabulum 65 comprises a first part 1841 adapted to be fixated to the femoral bone of the patient. The first part comprises an inner contacting surface adapted to be in movable connection with an outer contacting surface of a second part 1842. The second part 1842 is rotatably fixated to the first part 1841 by a rotatable connecting member 1843. An outer contacting surface of a prosthetic spherical portion 45 is adapted to be placed in contact with the inner surface of the second part 1842 and be movable in multiple directions, thus replicating the natural ball and socket joint of the hip. The second part 1842 comprises two extending portions 1823a,b extending beyond the equator line 1845 of the second part 1842. The extending portions 1823a,b extends longitudinally discontinuously along the equator line, thus creating an area between the extending portions, in which area a portion of the prosthetic elongated portion can be placed, thus being placed partially between the equator line 1845 and the extension line 1846. The construction shown in FIG. 26 enables the second part 1842 to rotate if the prosthetic elongated portion 2201 engages the extending portions 1823a,b, which are sloped for this purpose. This way the second part 1842 are always placed such that the prosthetic elongated portion 2201 can be placed partially between equator line 1845 and the extension line 1846, which creates an optimal range of movement whilst the second part clasps the prosthetic spherical portion 45, and thus restricting the spherical portion 45 in the second part 1842 of the prosthetic replacement for the acetabulum 65.

Figure 15A:
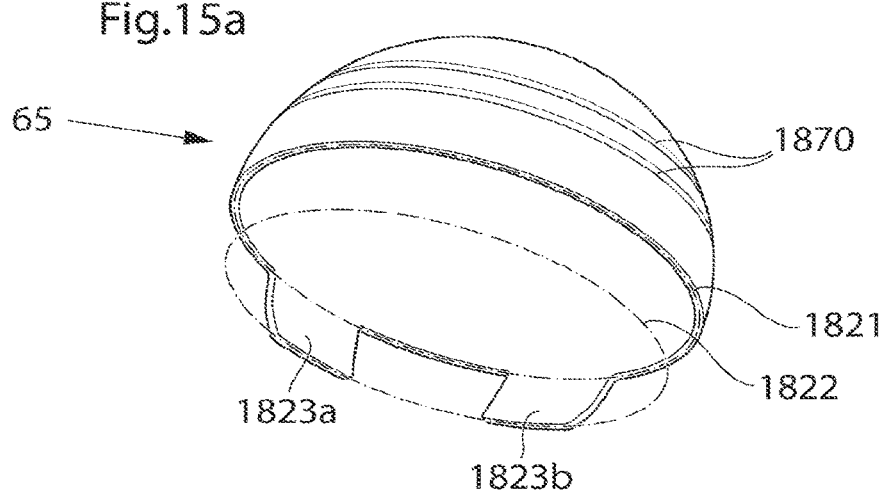
FIG. 15a-15f shows embodiments of prosthetic replacements for the acetabulum.

FIG. 15a shows the prosthetic replacement for the acetabulum 65 according to one embodiment n this embodiment the prosthetic replacement for the acetabulum 65 comprises two extending portions 1823a, b. The prosthetic replacement for the acetabulum 65 is according to this embodiment adapted to be fixated to the femoral bone by means of an adhesive which is adapted to be placed in connection with the adhesive recesses 1870 of the outer surface of the prosthetic replacement for the acetabulum 65.

Figure 15B:
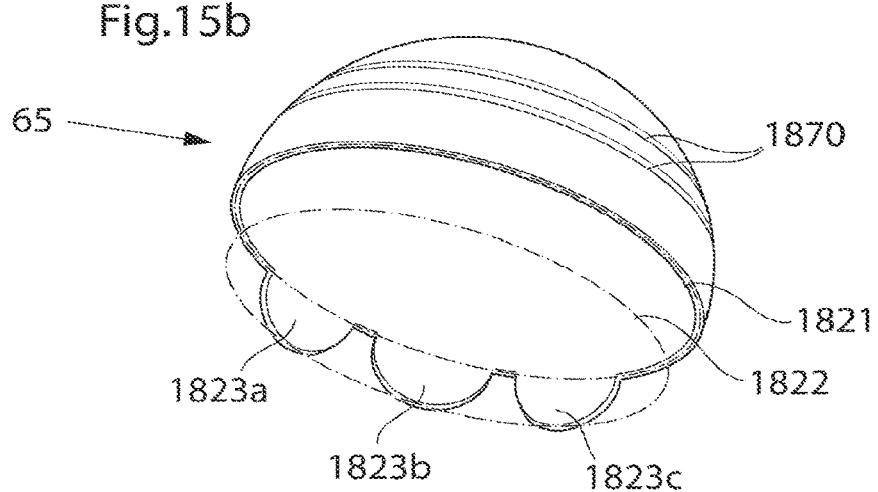

FIG. 15b shows a prosthetic replacement for the acetabulum 65 similar to the prosthetic replacement for the acetabulum 65 disclosed with reference to FIG. 15*a*, but with the difference that it comprises three equally extending portions 1823*a,b,c*.

Figure 15C:
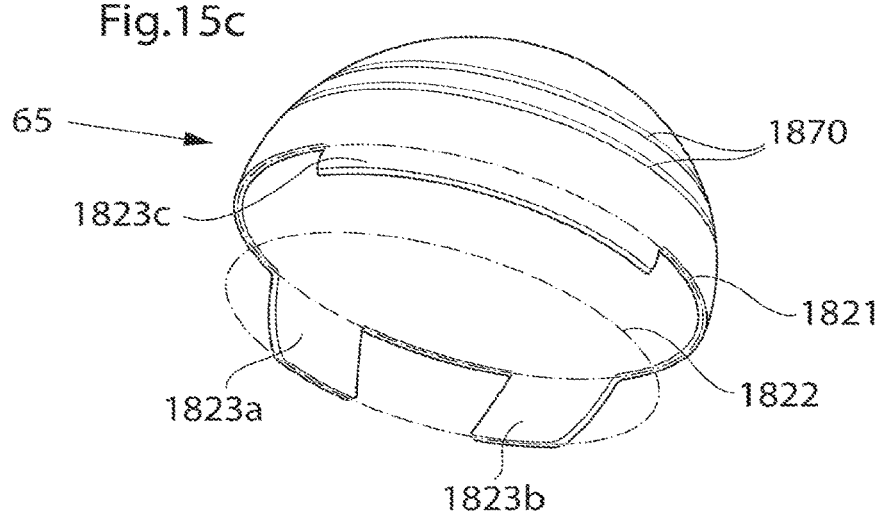

FIG. 15*c* shows a prosthetic replacement for the acetabulum 65, similar to the prosthetic replacement for the acetabulum 65 disclosed with reference to FIG. 15*a*, but with the difference that it comprises two equally extending portions 1823*a,b* and one less extending portion 1823*c*.

Figure 15D:
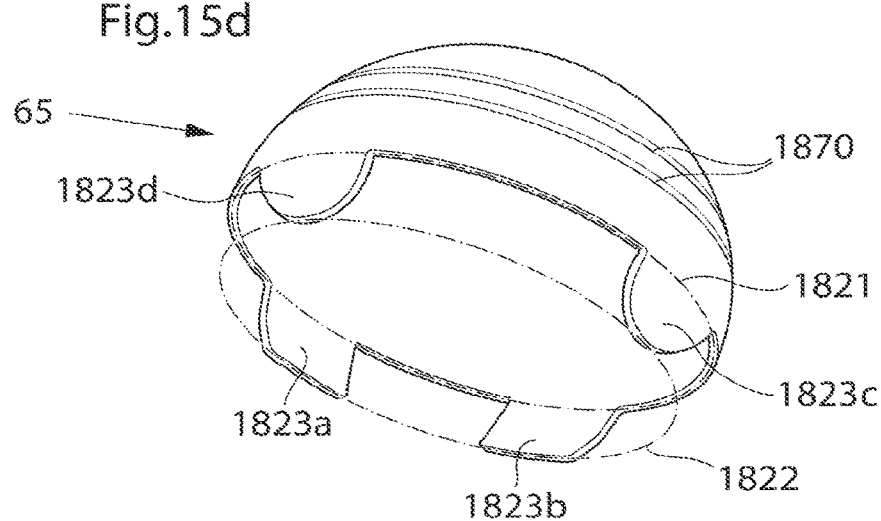

FIG. 15*d* shows a prosthetic replacement for the acetabulum 65 similar to the prosthetic replacement for the acetabulum 65 disclosed with reference to FIG. 15*a*, but with the difference that it comprises four equally extending portions 1823*a,b,c,d*.

Figure 15E:
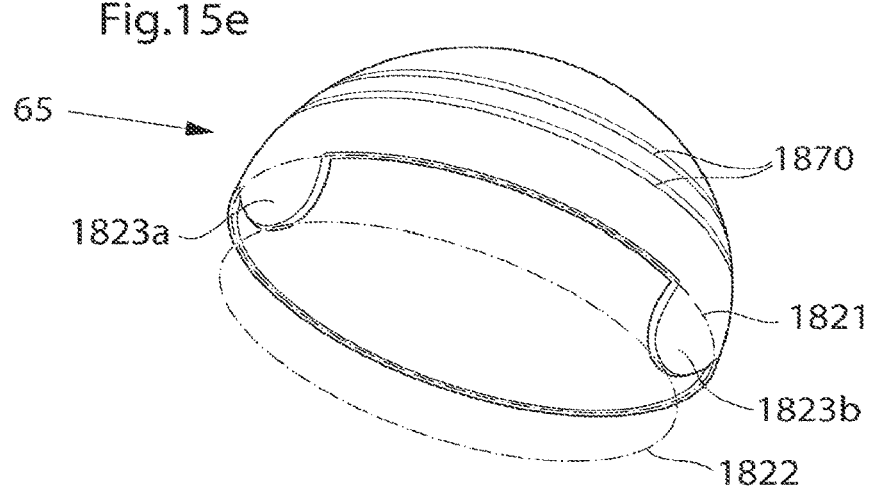

FIG. 15*e* shows a prosthetic replacement for the acetabulum 65 similar to the prosthetic replacement for the acetabulum 65 disclosed with reference to FIG. 15*a*, but with the difference that the two extending portions are placed further from each other, and thus being adapted to be placed in the proximal and distal quadrant, when implanted and being in the base position.

Figure 15F:
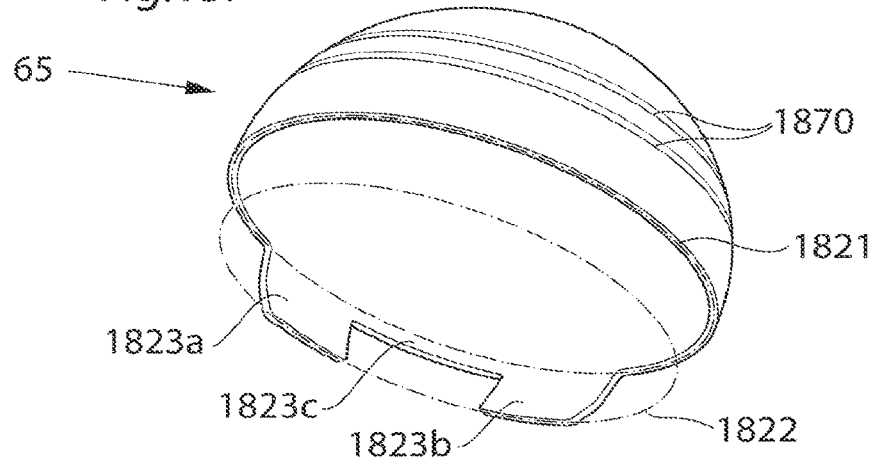

FIG. 15*f* shows a prosthetic replacement for the acetabulum 65 similar to the prosthetic replacement for the acetabulum 65 disclosed with reference to FIG. 15*a*, but further comprising a less extending portion 1823*c* placed between the first and second extending portions 1823*a,b*.

The extending portions of the prosthetic replacement for the acetabulum 65 which have been described could be made from an elastic material, enabling the extending portions to pass onto the a prosthetic spherical portion, according to any of the embodiments herein.

Figure 16A:
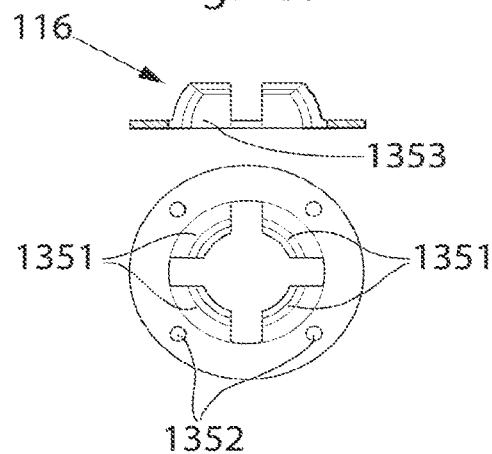
FIG. 16a shows an embodiment of the locking/releasing member.

FIG. 16*a* shows an embodiment of a locking/releasing member 116, wherein the locking/releasing member 116 comprises a surface 1353 adapted to be in contact with the artificial convex hip joint surface (replacement for the caput femur) (112 in FIG. 16*b*), being a first piece, and slide against the hip joint surface, the locking member 116 is adapted to, in a first state, lock the artificial caput femur 112 to the artificial acetabulum surface (1340 in FIG. 16*b*), and in a second state, release said artificial caput femur 112 from said artificial acetabulum 1340. The locking/releasing member 116 is adapted to change from the first the second state when a predetermined amount of strain is placed on the locking/releasing member 116. The locking/releasing member 116 comprises four holding members, here being elastic portions 1351, and the locking/releasing member 116 is adapted to change from the first t the second state using the elasticity of the elastic portions 1351. The locking member 116 is adapted to be fixated to the femoral bone 7 using screws adapted to be placed in holes 1352 adapted therefor. According to another embodiment (not shown) the holding members 1351 comprises at least one holding member adapted to roll against the first piece, being the artificial convex hip joint surface 112.

Figure 16B:
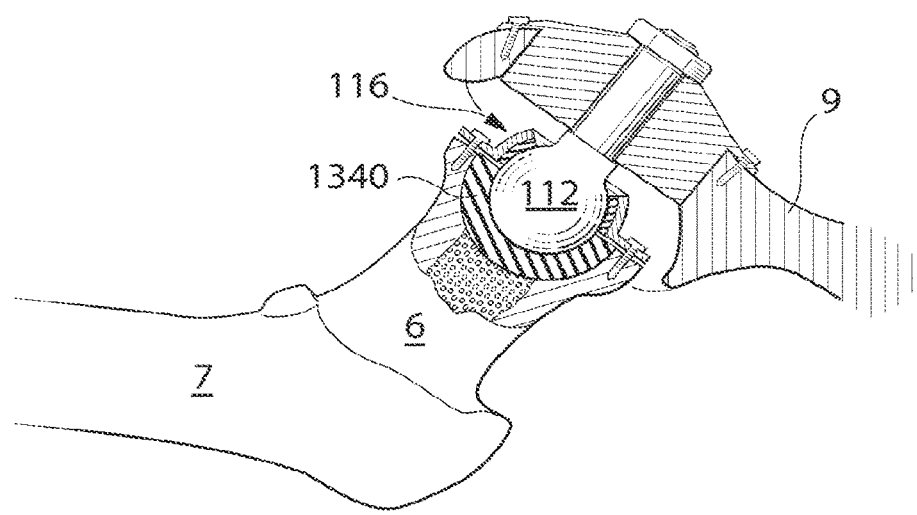
FIG. 16b shows the hip joint in section in an embodiment when the locking/releasing member locks an artificial caput femur in artificial acetabulum.

FIG. 16*b* shows the hip joint in section when the two state locking/releasing member 116 locks the artificial caput femur 112 in the artificial acetabulum 1340. The two state locking/releasing member 116 is fixated to the femoral bone 7 using screws 121, and is here shown in its first state in which the locking/releasing member 116 locks the artificial caput femur 112 to the artificial acetabulum 1340.

Figure 16C:
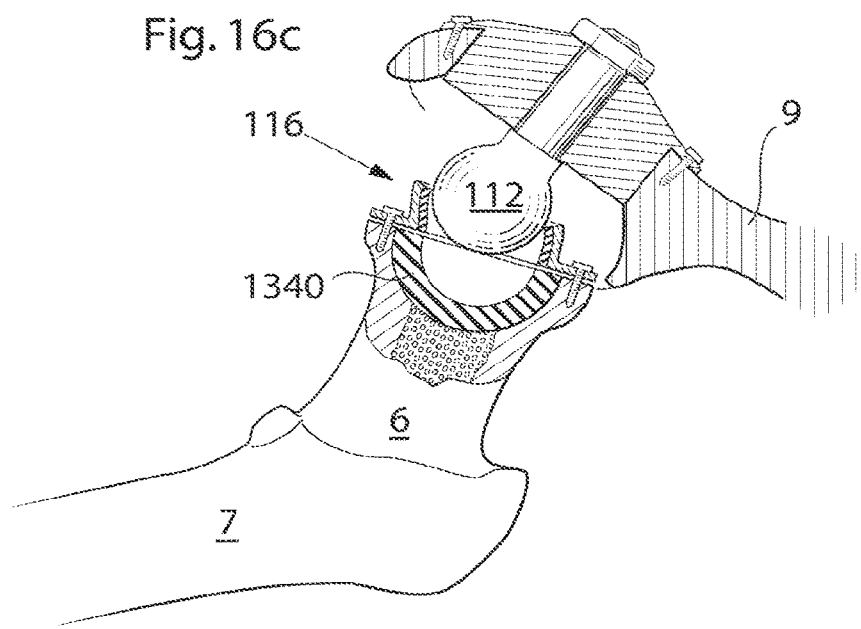
FIG. 16c shows the hip joint in section in an embodiment when the locking/releasing member releases the artificial caput femur from the artificial acetabulum.

FIG. 16*c* shows the hip joint in section according to the embodiment of FIG. 16*b*, but when the two state locking/releasing member 116 is in its second state, in which the locking/releasing member 116 releases the artificial caput femur 112 from the artificial acetabulum surface 1340. The construction with the locking/releasing member 116 reduces the risk of strain placed on the artificial joint injuring the fixation points, i.e. the contact with bone; it further enables the artificial joint to be non-invasively relocated in case of luxation.

Figure 16D:
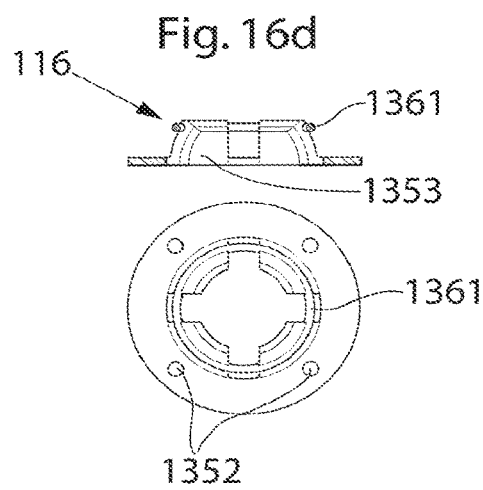
FIG. 16d shows another embodiment of the locking/releasing member.

FIG. 16*d* shows an alternative embodiment of the two-state locking/releasing member 116, in which the two-state locking/releasing member 116 further comprises an elastic band 1361 adapted to encircle the artificial caput femur 112, when implanted. The elastic band 1361 could be an elastic polymer band, such as a polyurethane or silicone band.

Figure 16E:
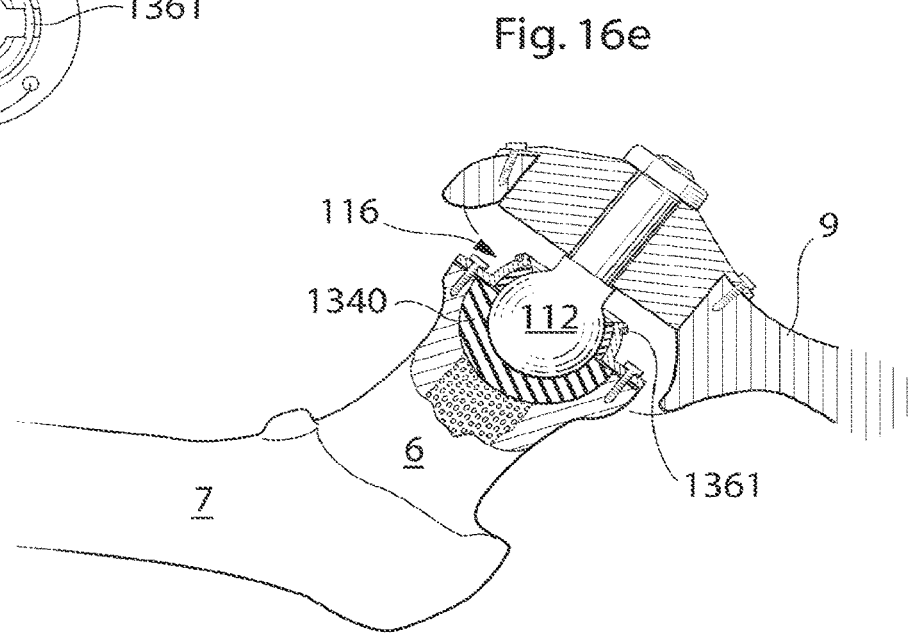
FIG. 16e shows the hip joint in section in an embodiment when the locking/releasing member locks the artificial caput femur to the artificial acetabulum.

FIG. 16*e* shows a hip joint in section when the two-state locking/releasing member 116 has been implanted, and being in its first state. The two-state locking/releasing member 116 is fixated to the femoral bone 7 using screws 121.

Figure 16F:
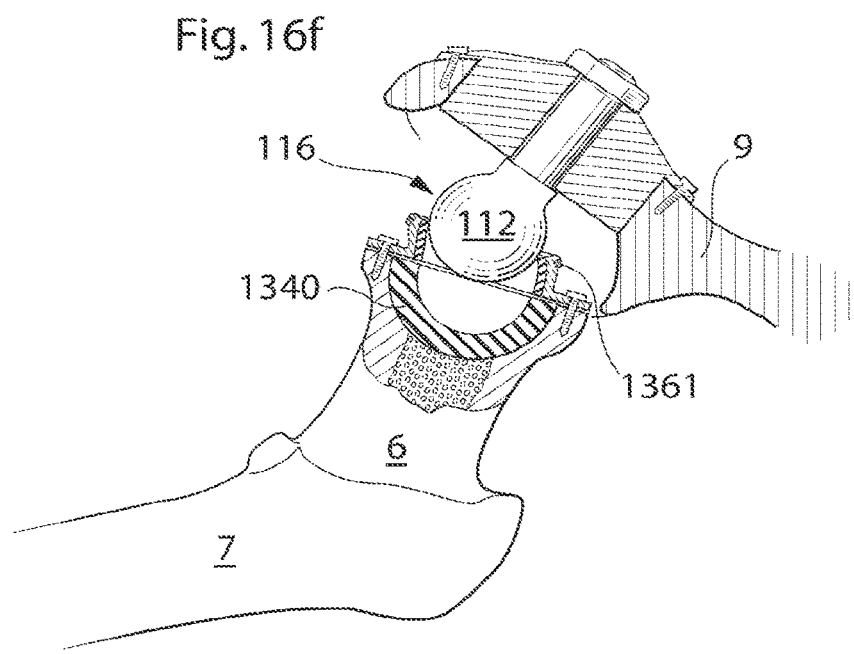
FIG. 16f shows the hip joint in section in an embodiment when the locking/releasing member releases the artificial caput femur from the artificial acetabulum.
Figure 16:
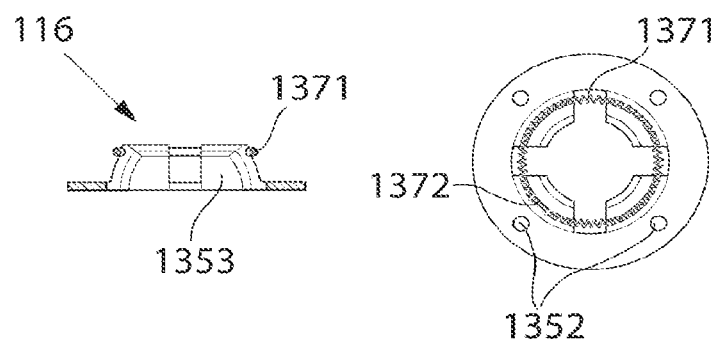
FIG. 16g shows another embodiment of the locking/releasing member.
FIG. 16h shows another embodiment of the locking/releasing member.
FIG. 16i shows the hip joint in section when an artificial hip joint is being assembled.
FIG. 16j shows the hip joint in section when an artificial hip joint is being assembled.
FIGS. 16k and 16l shows the hip joint in section when an artificial hip joint is assembled.
FIGS. 16m and 16n shows the hip joint in section according to the embodiment of FIG. 16k, when released.
Figure 16:
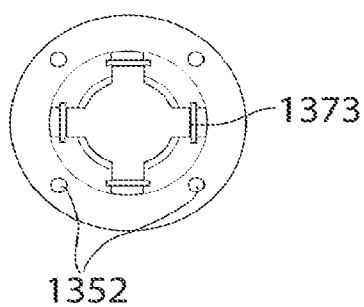
Figure 16:
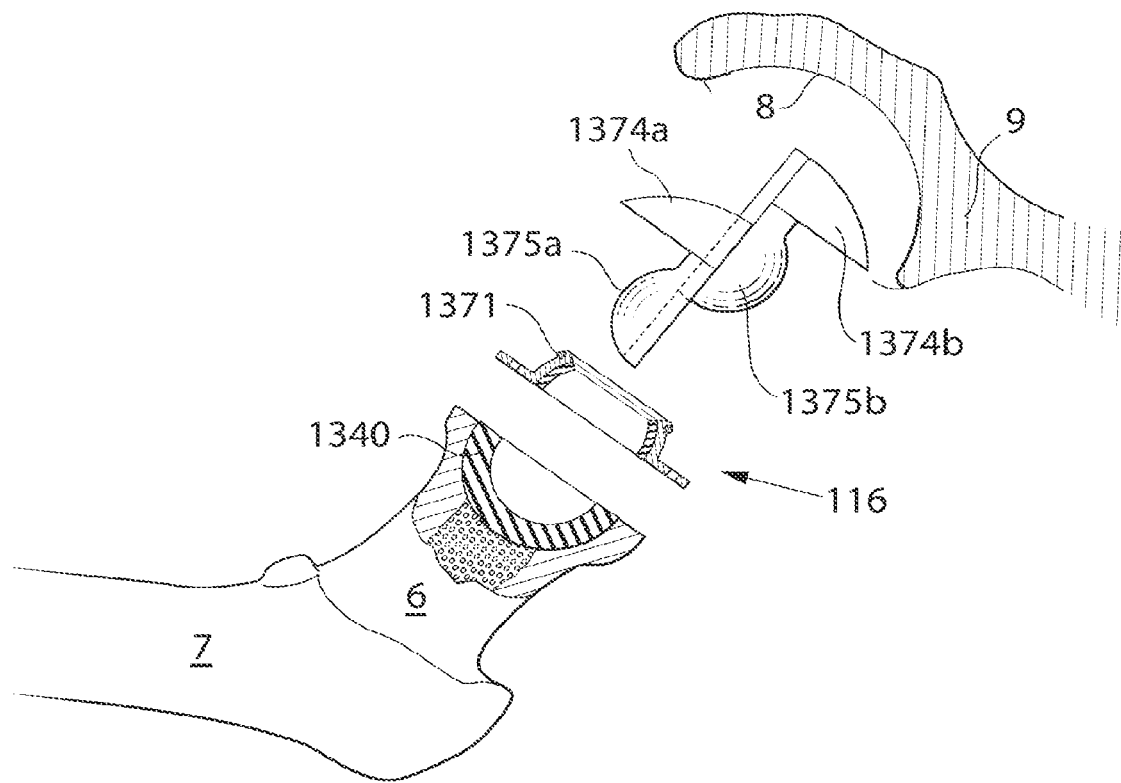

FIG. 16*f* shows the implantable device comprising the two-state locking/releasing member 116 when in its second state, i.e. in the state in which the locking/releasing member 116 is adapted to release the artificial caput femur 112 through the elastic band 1361 encircling the artificial caput femur 112 is stretched so that the artificial caput femur 112 can exit from the artificial acetabulum 1340. The construction with the locking/releasing member 116 reduces the risk of strain placed on the artificial joint injuring the fixation points, i.e. the contact with bone; it further enables the artificial joint to be non-invasively relocated in case of luxation.

The locking/releasing member 116 described with reference to FIGS. 16*a*-16*f* are depicted in embodiments with a large hole in the pelvic bone 9 occupied by a prosthetic part 118, however, it is equally conceivable that the two state locking/releasing member 116 is used in embodiments with a small hole in the pelvic bone 9, for a less invasive procedure, it is furthermore conceivable that the all of the embodiments disclosed of the medical device could be installed during conventional open hip joint surgical procedure, penetrating the hip joint capsule. In this case the two state locking/releasing member 116 could be a part of a full prosthesis.

FIG. 16*g* shows an embodiment of a locking/releasing member 116, wherein the locking/releasing member 116 comprises a spring 1371 creating the elasticity needed to change from a first state to a second state for releasing the artificial caput femur 112 from the artificial acetabulum 1340. The locking/releasing member 116 is adapted to change from the first to the second state when a predetermined amount of strain is placed on the locking/releasing member 116. According to the embodiment shown in FIG. 16*g* the medical device further comprises a calibration screw 1372 placed in connection with the spring 1371 for calibrating the elasticity and thereby the amount of strain required for the locking/releasing member to change from the first to the second state.

FIG. 16*h* shows an embodiment of the locking/releasing member in which the locking/releasing member comprises four rupture pins 1373 adapted to fail at a predetermined strain, for allowing the locking/releasing 116 members to change from the first to the second state. The pins are, according to this embodiment, made from a brittle material which could be adapted for the particular patient. In other embodiments (not shown) the rupture pins 1373 could be replaced by a rupture band, similar to the elastic band, but adapted to fail at a predetermined strain, or a rupture band placed centrally.

FIG. 16*i* shows the hip joint in section when an artificial caput femur 1375*a,b* comprising two parts 1375*a* and 1375*b* is adapted to be interconnected to form an interconnected artificial caput femur. Each of the two artificial parts 1375*a*, 1375*b*, furthermore comprises a fixating portion 1374*a*, 1374b adapted to be fixated to the inside of the acetabulum 8. The artificial caput femur is, after the interconnection, adapted to be placed in an artificial concave acetabulum 1340 placed in the proximal portion of the femoral bone 7, for creating a functional hip joint in an opposite embodiment.

Figure 16J:
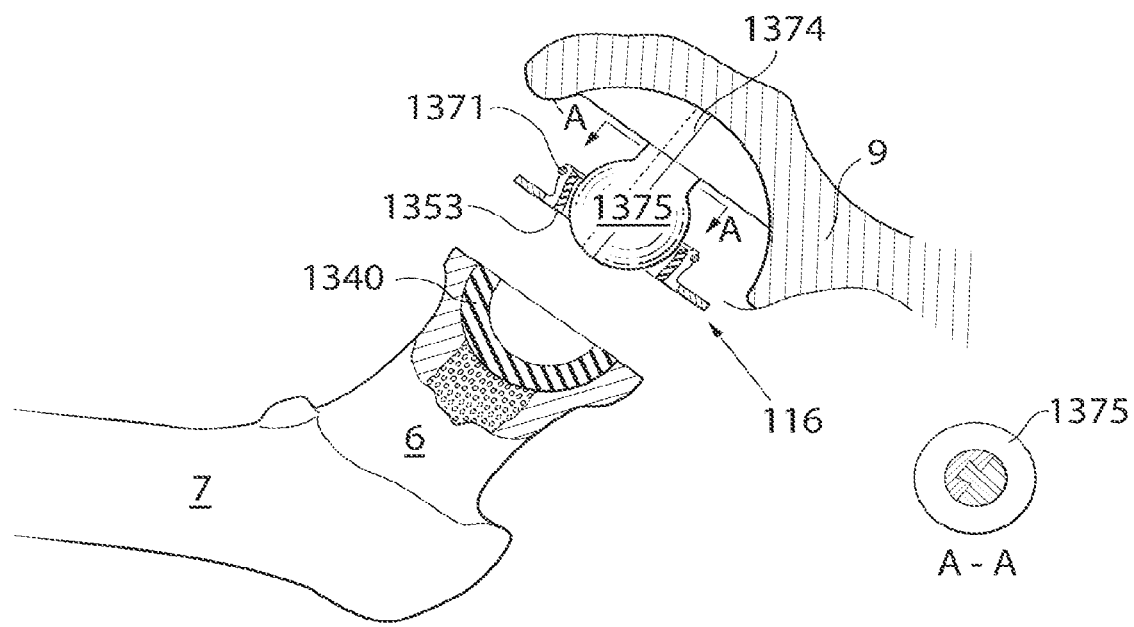

FIG. 16j shows the hip joint in section when the interconnected artificial caput femur 1375 has been placed in the acetabulum 8, and been fixated using the fixating portion 1374. The locking/releasing member 116 has been placed onto the artificial caput femur 1375 using the spring 1371 creating the elasticity required to enable the artificial caput femur 1375 to be placed such that the locking/releasing members clasps the artificial caput femur 1375.

Figure 16K:
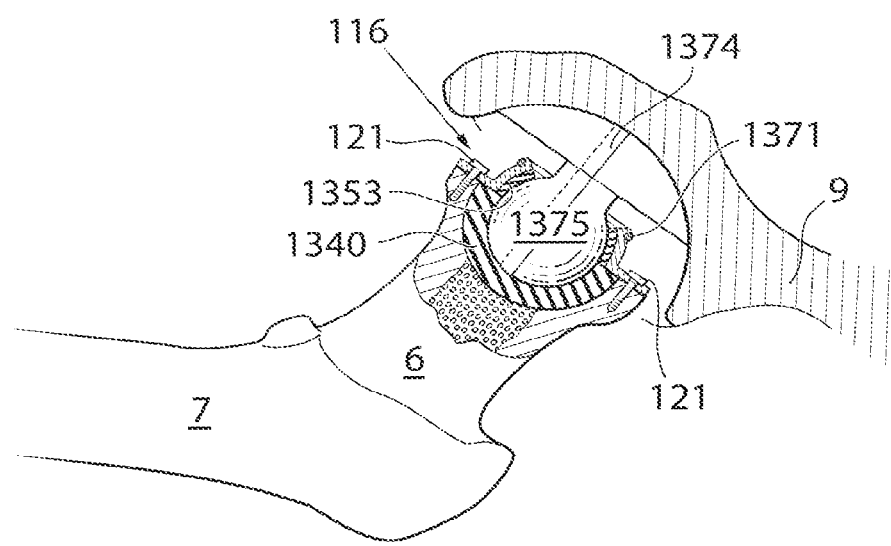
Figure 16:
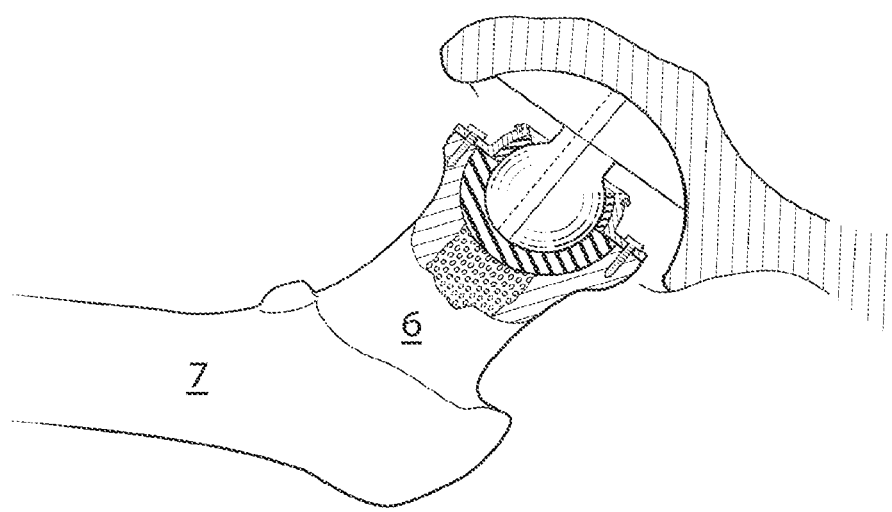
Figure 16:
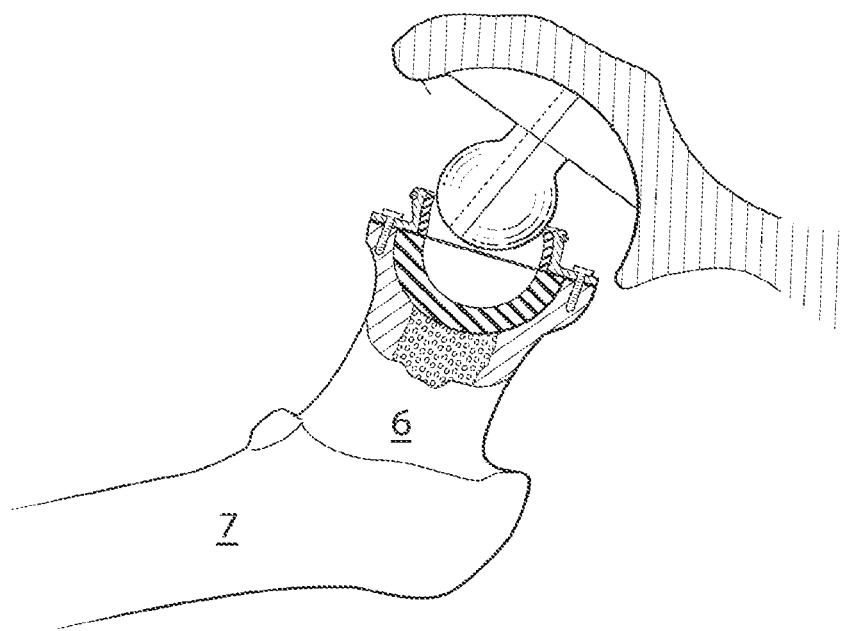
Figure 16:
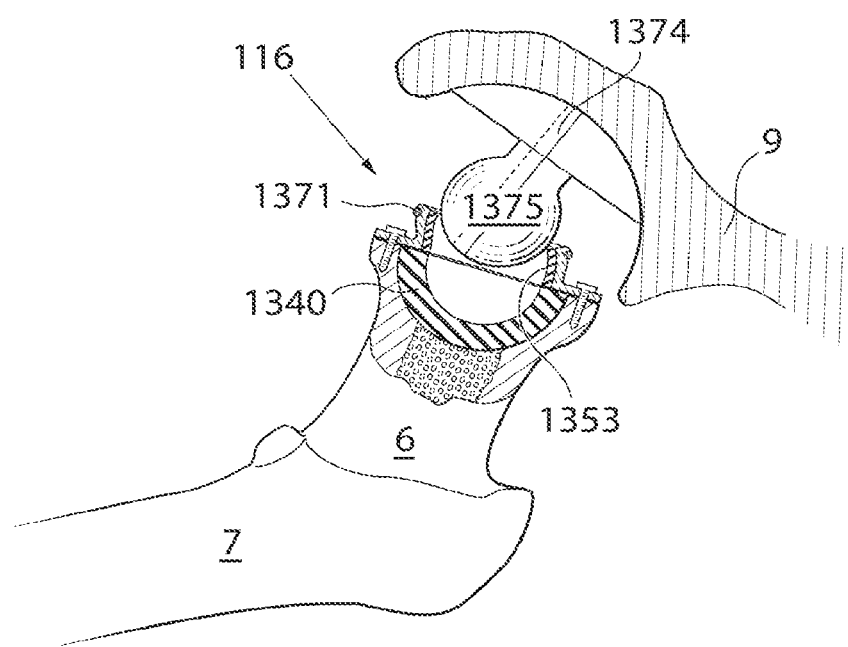

FIG. 16k shows the hip joint in section when the two state locking/releasing member 116 locks the interconnected artificial caput femur 1375 in the artificial acetabulum 1340. The two state locking/releasing member 116 is fixated to the femoral bone 7 using screws 121, and is here shown in its first state in which the locking/releasing member 116 locks the artificial caput femur 112 to the artificial acetabulum 1340.

FIGS. 16m and 16n shows the hip joint in section according to the embodiment of FIG. 16k, but when the two state locking/releasing member 116 is in its second state, in which the locking/releasing member 116 releases the artificial caput femur 112 from the artificial acetabulum surface 1340, by means of the spring 1371 creating the required elasticity. The construction with the locking/releasing member 116 reduces the risk of strain placed on the artificial joint injuring the fixation points, i.e. the contact with bone; it further enables the artificial joint to be non-invasively relocated in case of luxation.

Please note that any embodiment or part of embodiment as well as any method or part of method could be combined in any way. All examples herein should be seen as part of the general description and therefore possible to combine in any way in general terms.

The medical device according to any of the embodiments could comprise at least one material selected from a group consisting of: polytetrafluoroethylene (PIFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constant or intermittent lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms.

The invention claimed is:

1. A medical device for implantation in a hip joint of a patient, the medical device comprising a prosthetic replacement for the acetabulum, wherein the prosthetic replacement for the acetabulum comprises:
   a first part adapted to be fixated to the femoral bone of the patient; and
   a second part rotatably connected to the first part by means of a connecting member;
   wherein:
   the first part comprises a bowl-shaped inner contacting surface portion adapted to receive a bowl-shaped outer contacting surface portion of the second part such that the second part is rotatable, relative to the first part, around a point of rotation formed by the connecting member;
   the second part comprises a bowl-shaped inner surface adapted to receive a ball-shaped portion of a prosthetic replacement for the caput femur, adapted to be fixated to the pelvic bone, such that the prosthetic replacement for the caput femur and the second part form a ball joint in an opposite configuration; and
   the inner contacting surface of the second part comprises an equator line defining a largest circumference of the inner contacting surface, and at least one extending portion extending beyond the equator line and being adapted to clasp the ball-shaped portion of the prosthetic replacement for the caput femur.

2. The medical device according to claim 1, wherein the at least one extending portion is adapted to extend circumferentially along the equator line, dorsal to the right-left axis of pelvis when being in a defined base position.

3. The medical device according to claim 2, wherein the medical device comprises a second portion adapted to extend circumferentially along at least ½ of the equator line and not beyond the equator line.

4. The medical device according to claim 1, adapted to receive the ball-shaped portion of the prosthetic replacement for the caput femur, adapted to be fixated to the pelvic bone by means of an elongated member fixated to the ball-shaped portion of the prosthetic caput femur, wherein:
   the at least one extending portion extends beyond the equator line such that an end portion of the inner surface of the second part forms a circular extension line defining a smaller cross-sectional distance measured from a point in said end portion going through a geometrical center point and measured to an opposite portion of said second part than a diameter of the equator line; and
   the at least one extending portion circumferentially extends discontinuously along the equator line such that a portion of the elongated member can be placed between the extension line and the equator line, when the medical device is implanted together with the prosthetic replacement for the caput femur.

5. The medical device according to claim 4, wherein the medical device is adapted such that the extension line is placed dorsal to the equator line when the medical device is implanted.

6. The medical device according to claim 4, wherein the connecting member is adapted to allow the second part to rotate in response to the portion of the elongated member engaging the at least one extending portion.

7. The medical device according to claim 6, wherein the at least one extending portion comprises a sloped portion for allowing the portion of the elongated member to slide against the at least one extending portion.

8. The medical device according to claim 1, wherein at least a first portion of the medical device is an extending portion, extending beyond the equator line, and at least a second portion is a portion not extending beyond the equator line, wherein the first portion circumferentially extend in at least one of:
- along at least 1/10 of the equator line
- along at least 1/4 of the equator line;
- along at least 1/3 of the equator line; and
- along at least 1/2 of the equator line.

9. The medical device according to claim 1, wherein the second part is adapted to release the prosthetic caput femur from the medical device when a predetermined strain is placed on the hip joint.

10. The medical device according to claim 1, wherein the at least one extending portion, when implanted, is adapted to be placed such as to restrict the motion range of the hip joint, and wherein the at least one extending portion is adapted to be placed such that at least one of:
- adduction is restricted more degrees than flexion;
- abduction is restricted more degrees than flexion;
- adduction is restricted more degrees than extension;
- abduction is restricted more degrees than extension.

11. The medical device according to claim 1, further comprising a prosthetic replacement for the caput femur adapted to be received in the bowl-shaped inner surface of the second part, comprising a ball-shaped portion and an elongated member, and adapted to be fixated to the pelvic bone by means of the elongated member fixated to the ball-shaped portion.

12. The medical device according to claim 1, further comprising at least one hole adapted to receive a fixating member for fixating the medical device to the femoral bone.

13. The medical device according to claim 12, wherein the hole is adapted to receive a screw for fixating the medical device to the femoral bone.

14. The medical device according to claim 1, further comprising a locking member for in situ restraining the prosthetic replacement for the caput femur in the second part.

15. A method of implanting a prosthetic replacement for the acetabulum, the method comprising the steps of:
- cutting the skin of the patient,
- inserting a dissecting tool and dissecting an area of the hip joint,
- providing a prosthetic replacement for the acetabulum comprising:
  - a first part adapted to be fixated to the femoral bone of the patient; and
  - a second part rotatably connected to the first part by means of a connecting member, wherein:
  - the first part comprises a bowl-shaped inner contacting surface portion adapted to receive a bowl-shaped outer contacting surface portion of the second part such that the second part is rotatable, relative to the first part, around a point of rotation formed by the connecting member,
  - the second part comprises a bowl-shaped inner surface adapted to receive a ball-shaped portion of a prosthetic replacement for the caput femur, adapted to be fixated to the pelvic bone, such that the prosthetic replacement for the caput femur and the second part form a ball joint in an opposite configuration, and
  - the inner contacting surface of the second part comprises an equator line defining a largest circumference of the inner contacting surface, and at least one extending portion extending beyond the equator line and being adapted to clasp the ball-shaped portion of the prosthetic replacement for the caput femur, and
- fixating the first part to the femoral bone of the patient.

16. A method of implanting a prosthetic replacement for the acetabulum, the method comprising the steps of:
- inserting a tube into an area of a hip joint of a patient,
- using the tube to fill the area with a fluid thereby expanding the area,
- placing at least two trocars in the patient's body,
- inserting a camera through one of the trocars into the area,
- inserting a dissecting tool through any of the trocar and dissecting in the area,
- providing a prosthetic replacement for the acetabulum comprising:
  - a first part adapted to be fixated to the femoral bone of the patient; and
  - a second part rotatably connected to the first part by means of a connecting member, wherein:
  - the first part comprises a bowl-shaped inner contacting surface portion adapted to receive a bowl-shaped outer contacting surface portion of the second part such that the second part is rotatable, relative to the first part, around a point of rotation formed by the connecting member,
  - the second part comprises a bowl-shaped inner surface adapted to receive a ball-shaped portion of a prosthetic replacement for the caput femur, adapted to be fixated to the pelvic bone, such that the prosthetic replacement for the caput femur and the second part form a ball joint in an opposite configuration, and
  - the inner contacting surface of the second part comprises an equator line defining a largest circumference of the inner contacting surface, and at least one extending portion extending beyond the equator line and being adapted to clasp the ball-shaped portion of the prosthetic replacement for the caput femur, and
- fixating the first part to the femoral bone of the patient.

* * * * *